United States Patent [19]
Parce et al.

[11] Patent Number: 6,046,056
[45] Date of Patent: Apr. 4, 2000

[54] HIGH THROUGHPUT SCREENING ASSAY SYSTEMS IN MICROSCALE FLUIDIC DEVICES

[75] Inventors: J. Wallace Parce, Palo Alto; Anne R. Kopf-Sill, Portola Valley; Luc J. Bousse, Menlo Park, all of Calif.

[73] Assignee: Caliper Technologies Corporation, Palo Alto, Calif.

[21] Appl. No.: 08/761,575

[22] Filed: Dec. 6, 1996

Related U.S. Application Data

[63] Continuation-in-part of application No. 08/671,987, Jun. 28, 1996.

[51] Int. Cl.$^7$ .................. G01N 33/558; G01N 33/543
[52] U.S. Cl. .................. 436/514; 204/400; 204/403; 204/409; 204/412; 422/55; 422/57; 422/58; 422/82.01; 435/7.9; 435/287.1; 435/287.2; 435/288.3; 435/288.4; 435/288.7; 435/810; 436/149; 436/150; 436/151; 436/164; 436/165; 436/172; 436/518; 436/527; 436/531; 436/535; 436/805; 436/809
[58] Field of Search ........................... 422/55, 57, 58, 422/82.01; 435/7.9, 287.1, 287.2, 288.3, 288.4, 288.7, 810; 436/514, 518, 527, 531, 535, 149, 150, 151, 164, 165, 172, 805, 809; 204/400, 403, 409, 412

[56] References Cited

U.S. PATENT DOCUMENTS

| | | | |
|---|---|---|---|
| 4,675,300 | 6/1987 | Zare et al. | 436/172 |
| 4,908,112 | 3/1990 | Pace . | |
| 4,963,498 | 10/1990 | Hillman et al. . | |
| 4,978,503 | 12/1990 | Shanks et al. | 422/58 |
| 5,126,022 | 6/1992 | Soane et al. . | |
| 5,140,161 | 8/1992 | Hillman et al. . | |
| 5,144,139 | 9/1992 | Hillman et al. . | |
| 5,164,598 | 11/1992 | Hillman et al. . | |

(List continued on next page.)

FOREIGN PATENT DOCUMENTS

| | | | |
|---|---|---|---|
| 568 902 | 11/1993 | European Pat. Off. | F04B 43/04 |
| 637 998 | 7/1996 | European Pat. Off. | B01L 3/00 |
| 639 223 | 7/1996 | European Pat. Off. | C12M 3/00 |
| 2 248 891 | 4/1992 | United Kingdom | F04B 21/00 |
| WO 94/05414 | 3/1994 | WIPO . | |
| WO 95/12608 | 5/1995 | WIPO | C07K 1/04 |
| WO 95/27210 | 10/1995 | WIPO . | |
| WO 95/27211 | 10/1995 | WIPO . | |
| WO 95/33846 | 12/1995 | WIPO . | |
| WO 96 04547 | 2/1996 | WIPO . | |
| WO 96/04547 | 2/1996 | WIPO | G01N 27/00 |
| WO 96 15450 | 5/1996 | WIPO . | |
| WO 96 15576 | 5/1996 | WIPO . | |
| WO 96/14933 | 5/1996 | WIPO | B01L 3/00 |
| WO 96/14934 | 5/1996 | WIPO | B01L 3/00 |
| WO 96/15269 | 5/1996 | WIPO | C12Q 1/68 |
| WO 97/02357 | 1/1997 | WIPO . | |
| WO 97/22000 | 6/1997 | WIPO | G01N 33/50 |
| WO 98/05959 | 2/1998 | WIPO | G01N 33/50 |

OTHER PUBLICATIONS

Jacobson, et al., "Open channel electrochromatography on a microchip," *Anal. Chem.,* 66:2369–2373 (1994).

Kounty et al., Microchip Electrophoretic Immunoasay for Serum Cortisol, *Anal. Chem.* 68: 18–22 (1996).

Schmalzing et al., Solution–Phase Immunoassay for Determination of Cortisol in Serum by Capillary Electrophoresis, *Clin. Chem.* 41: (9) 1403–1406 (1995).

(List continued on next page.)

*Primary Examiner*—Christopher L. Chin
*Attorney, Agent, or Firm*—Townsend and Townsend and Crew, LLP; Matthew B. Murphy; Jonathan Alan Quine

[57] ABSTRACT

The present invention provides novel microfluidic devices and methods that are useful for performing high-throughput screening assays. In particular, the devices and methods of the invention are useful in screening large numbers of different compounds for their effects on a variety of chemical, and preferably, biochemical systems.

38 Claims, 17 Drawing Sheets

U.S. PATENT DOCUMENTS

| | | |
|---|---|---|
| 5,171,132 | 12/1992 | Miyazaki et al. . |
| 5,171,534 | 12/1992 | Smith et al. . |
| 5,188,963 | 2/1993 | Stapleton . |
| 5,192,405 | 3/1993 | Petersen et al. . |
| 5,271,724 | 12/1993 | van Lintel . |
| 5,277,556 | 1/1994 | van Lintel . |
| 5,296,375 | 3/1994 | Kricka et al. . |
| 5,304,487 | 4/1994 | Wilding et al. ............................ 422/55 |
| 5,375,979 | 12/1994 | Trah . |
| 5,427,946 | 6/1995 | Kricka et al. . |
| 5,486,335 | 1/1996 | Wilding et al. ............................ 422/58 |
| 5,498,392 | 3/1996 | Wilding et al. . |
| 5,571,410 | 11/1996 | Swedberg . |
| 5,585,069 | 12/1996 | Zanzucchi et al. . |
| 5,593,838 | 1/1997 | Zanzucchi et al. . |
| 5,605,662 | 2/1997 | Heller et al. ............................ 422/68.1 |
| 5,637,469 | 6/1997 | Wilding et al. ......................... 435/7.21 |
| 5,773,298 | 6/1998 | Lynggaard et al. . |
| 5,780,754 | 7/1998 | Karlberg et al. . |

OTHER PUBLICATIONS

J C Weaver et al.: "Gel microdroplets: Rapid detection & enumeration of individual microorganisms by their metabolic activity" Bio/Technology, vol. 6, Sep. 1988, pp. 1084–1089, XP002044138.

Chu et al., Affinity Capillary Electrophoresis–Mass Spectrometry for Screening Combinatorial Libraries, *J. Am. Chem. Soc.,* 18, 7827–7835.

Chu et al., Affinity Capillary Electrophoresis–Mass Spectrometry for Screening Combinatorial Libraries, *J. Am. Chem. Soc.,* 118, 7827–7835 (1996).

Jacobson et al., Fused Quartz Substrats for Microchip Electrophoresis, *Anal Chem. 1995,* 67:13 pp. 2059–2063.

Bao, et al., J. Chromatog. 608:217–224 (1992), Ultramicro Enzyme Assays in a Capillary Electrophoretic System.

Harmon, et al., Anal. Chem. 65:2655–2662 (1993), Mathematical Treatment of Electrophoretically Mediated Microanalysis.

Harmon, et al., Anal. Chem. 66:3797–3805 (1994), Selectivity in Electrophoretically Mediated Microanalysis by Control of Product Detection Time.

Manz, et al., J. Micromech. Microeng. 4:257–265 (1994), Electroosmotic Pumping and Electrophoretic Separations for Miniaturized Chemical Analysis Systems.

Manz, et al., Trends in Anal. Chem. 10(5):144–149 (1991), Micromachining of Monocrystalline Silicon and Glass for Chemical Analysis Systems.

Ramsey, et al., Nature Med. 1(10):1093 (1995), Microfabricated Chemical Measurement Systems.

Woolley, et al., PNAS 91:11348–352 (1994), Ultra–High––Speed DNA Fragment Separations Using Microfabricated Capillary Array Electrophoresis Chips.

Bunin & Ellman, "A General and Expedient Method for the Solid–Phase Synthesis of 1,4–Benzodiazepine Derivatives," *J. Amer. Chem. Soc.,* 114:10997–10998 (1992).

Cho et al., "An Unnatural Biopolymer," *Science,* 261:1303–1305 (1993).

Dasgupta & Liu, "Electroosmosis: A Reliable Fluid Propulsion System for Flow Injection Analysis," *Anal. Chem.,* 66, 1792–1798 (1994).

Harrison et al., "Capillary Electrophoresis and Sample Injection Systems Integrated on a Planar Glass Chip," *Anal. Chem.,* 65:1926–1932 (1992).

Harrison et al., "Micromachining a Miniaturized Capillary Electorphoresis–Based Chemical Analysis System on a Chip," *Science,* 261:895–897 (1993).

Jacobson et al., "Effects of Injection Schemes and Column Geometry on the Performance of Microchip Electrophoresis Devices," *Anal. Chem.,* 66:1107–1113 (1994).

Jacobson et al., "High–SpEed Separations on a Microchip," *Anal. Chem.,* 66:1114–1118 (1994).

Jung & Beck–Sickinger, "Multiple Peptide Synthesis Methods and Their Applications," *Angew. Chem. Int. Ed. Engl.,* 31(4):367–383 (1992).

Linhares & Kissinger, "Use of an On–Column Fracture in Capillary Zone Electrophoresis for Sample Introduction," *Anal. Chem.,* 63:2076–2078 (1991).

Manz et al., "Miniaturized Total Chemical Analysis Systems: a Novel Concept for Chemical Sensing," *Sensors and Actuators,* B1:244–248 (1990).

Manz et al., "Micromachining of monocrystalline silicon and glass for chemical analysis systems," *Trends in Analytical Chemistry,* 10(5):144–149 (1991).

Pavia et al., "The Generation of Molecular Diversity," *Bioorg. Med. Chem. Lett,* 3(3):387–396 (1993).

Seiler et al., "Planar Glass Chips for Capillary Electrophoresis: Repetitive Sample Injection, Quantitation, and Separation Efficiency," *Anal. Chem.,* 65:1481–1488 (1993).

Seiler et al., "Electoosmotic Pumping and Valveless Control of Fluid Flow within a Manifold of Capillaries on a Glass Chip," *Anal. Chem.,* 66:3485–3491 (1994).

Simon et al., "Peptoids: A modular approach to drug discovery," *PNAS,* 89:9367–9371 (1992).

Weaver et al., "Gel microdroplets: Rapid detection and enumeration of individual microorganisms by their metabolic activity," *Bio/Technology,* 6:1084–1089 (1988).

Wiley & Rich, "Peptidomimetics derived from Natural Products," *Med. Res. Rev.,* 13:327–384 (1993).

Zuckermann et al., "Efficient Method for the Preparation of Peptoids [Oligo(N–substituted glycines)] by Submonomer Solid–Phase Synthesis," *J. Amer. Chem. Soc.,* 114:10646–10647 (1992).

HIGH THROUGHPUT SCREENING ASSAY SYSTEMS IN MICROSCALE FLUIDIC DEVICES

CROSS-REFERENCE TO RELATED APPLICATIONS

This is a continuation-in-part of U.S. patent application Ser. No. 08/671,987 filed Jun. 28, 1996, which is hereby incorporated herein by reference in its entirety for all purposes.

BACKGROUND OF THE INVENTION

There has long been a need for the ability to rapidly assay compounds for their effects on various biological processes. For example, enzymologists have long sought better substrates, better inhibitors or better catalysts for enzymatic reactions. Similarly, in the pharmaceutical industries, attention has been focused on identifying compounds that may block, reduce, or even enhance the interactions between biological molecules. Specifically, in biological systems, the interaction between a receptor and its ligand often may result, either directly or through some downstream event, in either a deleterious or beneficial effect on that system, and consequently, on a patient for whom treatment is sought. Accordingly, researchers have long sought after compounds or mixtures of compounds that can reduce, block or even enhance that interaction.

Modern drug discovery is limited by the throughput of the assays that are used to screen compounds that possess these described effects. In particular, screening of the maximum number of different compounds necessitates reducing the time and labor requirements associated with each screen.

High throughput screening of collections of chemically synthesized molecules and of natural products (such as microbial fermentation broths) has thus played a central role in the search for lead compounds for the development of new pharmacological agents. The remarkable surge of interest in combinatorial chemistry and the associated technologies for generating and evaluating molecular diversity represent significant milestones in the evolution of this paradigm of drug discovery. See Pavia et al., 1993, *Bioorg. Med. Chem. Lett.* 3: 387–396, incorporated herein by reference. To date, peptide chemistry has been the principle vehicle for exploring the utility of combinatorial methods in ligand identification. See Jung & Beck-Sickinger, 1992, *Angew. Chem. Int. Ed. Engl.* 31: 367–383, incorporated herein by reference. This may be ascribed to the availability of a large and structurally diverse range of amino acid monomers, a relatively generic, high-yielding solid phase coupling chemistry and the synergy with biological approaches for generating recombinant peptide libraries. Moreover, the potent and specific biological activities of many low molecular weight peptides make these molecules attractive starting points for therapeutic drug discovery. See Hirschmann, 1991, *Angew. Chem. Int. Ed. Engl.* 30: 1278–1301, and Wiley & Rich, 1993, *Med. Res. Rev.* 13: 327–384, each of which is incorporated herein by reference. Unfavorable pharmacodynamic properties such as poor oral bioavailability and rapid clearance in vivo have limited the more widespread development of peptidic compounds as drugs however. This realization has recently inspired workers to extend the concepts of combinatorial organic synthesis beyond peptide chemistry to create libraries of known pharmacophores like benzodiazepines (see Bunin & Ellman, 1992, *J. Amer. Chem. Soc.* 114: 10997–10998, incorporated herein by reference) as well as polymeric molecules such as oligomeric N-substituted glycines ("peptoids") and oligo-carbamates. See Simon et al., 1992, *Proc. Natl. Acad. Sci. USA* 89: 9367–9371; Zuckermann et al., 1992, *J. Amer. Chem. Soc.* 114: 10646–10647; and Cho et al., 1993, *Science* 261:1303–1305, each of which is incorporated herein by reference.

In similar developments, much as modern combinatorial chemistry has resulted in a dramatic increase in the number of test compounds that may be screened, human genome research has also uncovered large numbers of new target molecules against which the efficacy of test compounds may be screened.

Despite the improvements achieved using parallel screening methods and other technological advances, such as robotics and high throughput detection systems, current screening methods still have a number of associated problems. For example, screening large numbers of samples using existing parallel screening methods have high space requirements to accommodate the samples and equipment, e.g., robotics, etc., high costs associated with that equipment, and high reagent requirements necessary for performing the assays. Additionally, in many cases, reaction volumes must be very small to account for the small amounts of the test compounds that are available. Such small volumes compound errors associated with fluid handling and measurement, e.g., evaporation. Additionally, fluid handling equipment and methods have typically been unable to handle these volume ranges with any acceptable level of accuracy due in part to surface tension effects in such small volumes.

The development of systems to address these problems must consider a variety of aspects of the assay process. Such aspects include target and compound sources, test compound and target handling, specific assay requirements, and data acquisition, reduction storage and analysis. In particular, there exists a need for high throughput screening methods and associated equipment and devices that are capable of performing repeated, accurate assay screens, and operating at very small volumes.

The present invention meets these and a variety of other needs. In particular, the present invention provides novel methods and apparatuses for performing screening assays which address and provide meaningful solutions to these problems.

SUMMARY OF THE INVENTION

The present invention generally provides methods of screening a plurality of test compounds for an effect on a biochemical system. These methods typically utilize microfabricated substrates which have at least a first surface, and at least two intersecting channels fabricated into that first surface. At least one of the intersecting channels will have at least one cross-sectional dimension in a range from 0.1 to 500 µm. The methods involve flowing a first component of a biochemical system in a first of the at least two intersecting channels. At least a first test compound is flowed from a second channel into the first channel whereby the test compound contacts the first component of the biochemical system. An effect of the test compound on the biochemical system is then detected.

In a related aspect, the method comprises continuously flowing the first component of a biochemical system in the first channel of the at least two intersecting channels. Different test compounds are periodically introduced into the first channel from a second channel. The effect, if any, of the test compound on the biochemical system is then detected.

In an alternative aspect the methods utilize a substrate having at least a first surface with a plurality of reaction channels fabricated into the first surface. Each of the plurality of reaction channels is fluidly connected to at least two transverse channels also fabricated in the surface. The at least first component of a biochemical system is introduced into the plurality of reaction channels, and a plurality of different test compounds is flowed through at least one of the at least two transverse channels. Further, each of the plurality of test compounds is introduced into the transverse channel in a discrete volume. Each of the plurality of different test compounds is directed into a separate reaction channel and the effect of each of the test compounds on the biochemical system is then detected.

The present invention also provides apparatuses for practicing the above methods. In one aspect, the present invention provides an apparatus for screening test compounds for an effect on a biochemical system. The device comprises a substrate having at least one surface with at least two intersecting channels fabricated into the surface. The at least two intersecting channels have at least one cross-sectional dimension in the range from about 0.1 to about 500 µm. The device also comprises a source of different test compounds fluidly connected to a first of the at least two intersecting channels, and a source of at least one component of the biochemical system fluidly connected to a second of the at least two intersecting channels. Also included are fluid direction systems for flowing the at least one component within the intersecting channels, and for introducing the different test compounds from the first to the second of the intersecting channels. The apparatus also comprises a detection zone in the second channel for detecting an effect of said test compound on said biochemical system.

In preferred aspects, the apparatus of the invention includes a fluid direction system which comprises at least three electrodes, each electrode being in electrical contact with the at least two intersecting channels on a different side of an intersection formed by the at least two intersecting channels. The fluid direction system also includes a control system for concomitantly applying a variable voltage at each of the electrodes, whereby movement of the test compounds or the at least first component in the at least two intersecting channels may be controlled.

In another aspect, the present invention provides an apparatus for detecting an effect of a test compound on a biochemical system, comprising a substrate having at least one surface with a plurality of reaction channels fabricated into the surface. The apparatus also has at least two transverse channels fabricated into the surface, wherein each of the plurality of reaction channels is fluidly connected to a first of the at least two transverse channels at a first point in each of the reaction channels, and fluidly connected to a second transverse channel at a second point in each of the reaction channels. The apparatus further includes a source of at least one component of the biochemical system fluidly connected to each of the reaction channels, a source of test compounds fluidly connected to the first of the transverse channels, and a fluid direction system for controlling movement of the test compound and the first component within the transverse channels and the plurality reaction channels. As above, the apparatuses also include a detection zone in the second transverse channel for detecting an effect of the test compound on the biochemical system.

BRIEF DESCRIPTION OF THE DRAWINGS

FIG. 2A shows a system used for screening effectors of an enzyme-substrate interaction. FIG. 2B illustrates the use of the apparatus in screening effectors of receptor-ligand interactions.

FIG. 9 shows fluorescence data from a continuous flow assay screen.

DESCRIPTION OF THE PREFERRED EMBODIMENT

Figure 1:
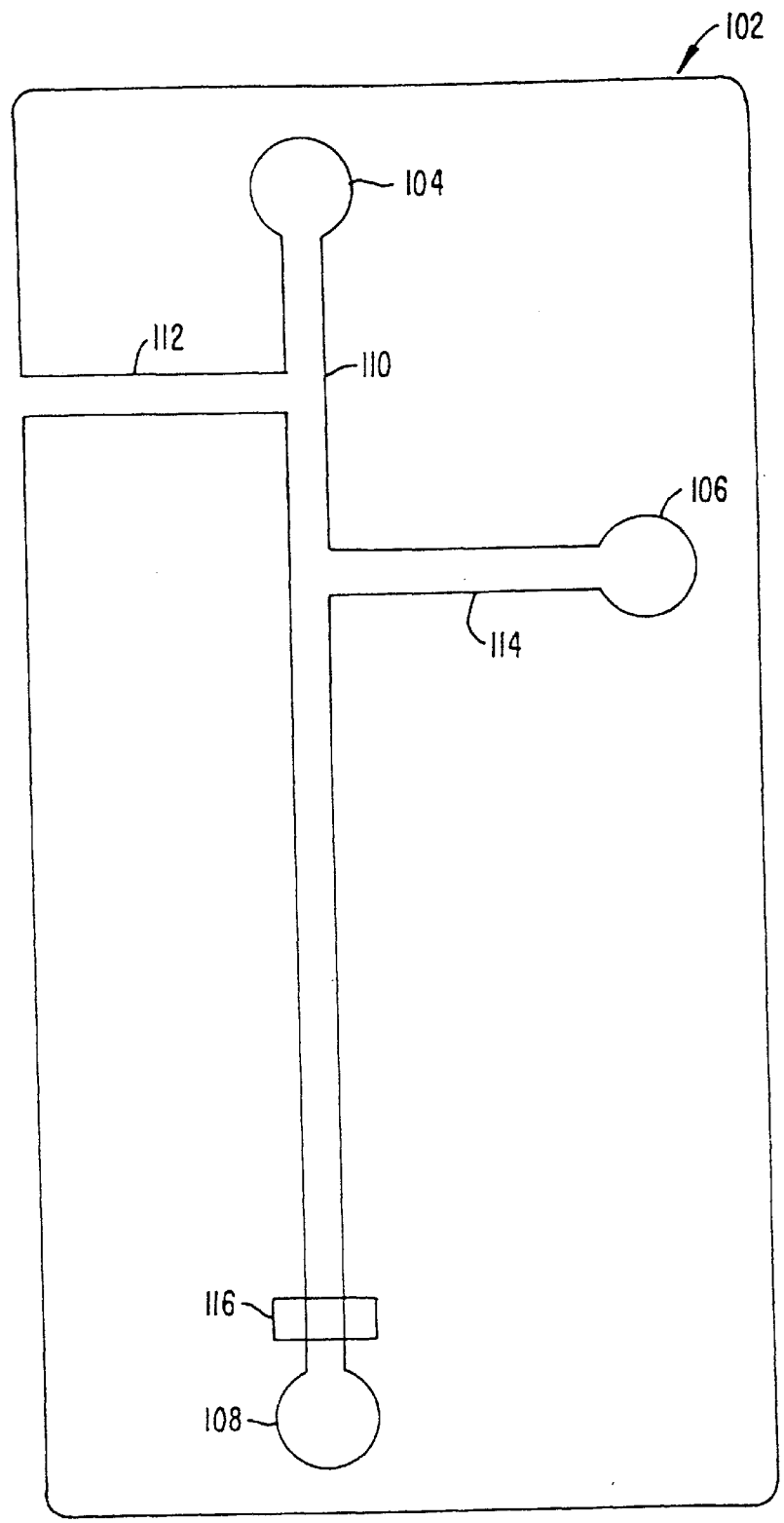
FIG. 1 is a schematic illustration of one embodiment of a microlaboratory screening assay system of the present invention which can be used in running a continuous flow assay system.

I. General The present invention provides novel microlaboratory systems and methods that are useful for performing high-throughput screening assays. In particular, the present invention provides microfluidic devices and methods of using such devices in screening large numbers of different compounds for their effects on a variety of chemical, and preferably, biochemical systems.

As used herein, the phrase "biochemical system" generally refers to a chemical interaction that involves molecules of the type generally found within living organisms. Such interactions include the full range of catabolic and anabolic reactions which occur in living systems including enzymatic, binding, signalling and other reactions. Further, biochemical systems, as defined herein, will also include model systems which are mimetic of a particular biochemical interaction. Examples of biochemical systems of particular interest in practicing the present invention include, e.g., receptor-ligand interactions, enzyme-substrate interactions, cellular signaling pathways, transport reactions involving model barrier systems (e.g., cells or membrane fractions) for bioavailability screening, and a variety of other general systems. Cellular or organismal viability or activity may also be screened using the methods and apparatuses of the present invention, i.e., in toxicology studies.

In order to provide methods and devices for screening compounds for effects on biochemical systems, the present invention generally incorporates model in vitro systems which mimic a given biochemical system in vivo for which effector compounds are desired. The range of systems against which compounds can be screened and for which effector compounds are desired, is extensive. For example, compounds may be screened for effects in blocking, slowing or otherwise inhibiting key events associated with biochemical systems whose effect is undesirable. For example, test compounds may be screened for their ability to block systems that are responsible, at least in part, for the onset of disease or for the occurrence of particular symptoms of diseases, including, e.g., hereditary diseases, cancer, bacterial or viral infections and the like. Compounds which show promising results in these screening assay methods can then be subjected to further testing to identify effective pharmacological agents for the treatment of disease or symptoms of a disease.

Alternatively, compounds can be screened for their ability to stimulate, enhance or otherwise induce biochemical systems whose function is believed to be desirable, e.g., to remedy existing deficiencies in a patient.

Once a model system is selected, batteries of test compounds can then be applied against these model systems. By identifying those test compounds that have an effect on the particular biochemical system, in vitro, one can identify potential effectors of that system, in vivo.

In their simplest forms, the biochemical system models employed in the methods and apparatuses of the present invention will screen for an effect of a test compound on an interaction between two components of a biochemical system, e.g., receptor-ligand interaction, enzyme-substrate interaction, and the like. In this form, the biochemical system model will typically include the two normally interacting components of the system for which an effector is sought, e.g., the receptor and its ligand or the enzyme and its substrate.

Determining whether a test compound has an effect on this interaction then involves contacting the system with the test compound and assaying for the functioning of the system, e.g., receptor-ligand binding or substrate turnover. The assayed function is then compared to a control, e.g., the same reaction in the absence of the test compound or in the presence of a known effector. Typically, such assays involve the measurement of a parameter of the biochemical system. By "parameter of the biochemical system" is meant some measurable evidence of the system's functioning, e.g., the presence or absence of a labeled group or a change in molecular weight (e.g., in binding reactions, transport screens), the presence or absence of a reaction product or substrate (in substrate turnover measurements), or an alteration in electrophoretic mobility (typically detected by a change in elution time of a labeled compound).

Although described in terms of two-component biochemical systems, the methods and apparatuses may also be used to screen for effectors of much more complex systems, where the result or end product of the system is known and assayable at some level, e.g., enzymatic pathways, cell signaling pathways and the like. Alternatively, the methods and apparatuses described herein may be used to screen for compounds that interact with a single component of a biochemical system, e.g., compounds that specifically bind to a particular biochemical compound, e.g., a receptor, ligand, enzyme, nucleic acid, structural macromolecule, etc.

Biochemical system models may also be embodied in whole cell systems. For example, where one is seeking to screen test compounds for an effect on a cellular response, whole cells may be utilized. Modified cell systems may also be employed in the screening systems encompassed herein. For example, chimeric reporter systems may be employed as indicators of an effect of a test compound on a particular biochemical system. Chimeric reporter systems typically incorporate a heterogenous reporter system integrated into a signaling pathway which signals the binding of a receptor to its ligand. For example, a receptor may be fused to a heterologous protein, e.g., an enzyme whose activity is readily assayable. Activation of the receptor by ligand binding then activates the heterologous protein which then allows for detection. Thus, the surrogate reporter system produces an event or signal which is readily detectable, thereby providing an assay for receptor/ligand binding. Examples of such chimeric reporter systems have been previously described in the art.

Additionally, where one is screening for bioavailability, e.g., transport, biological barriers may be included. The term "biological barriers" generally refers to cellular or membranous layers within biological systems, or synthetic models thereof. Examples of such biological barriers include the epithelial and endothelial layers, e.g. vascular endothelia and the like.

Biological responses are often triggered and/or controlled by the binding of a receptor to its ligand. For example, interaction of growth factors, i.e., EGF, FGF, PDGF, etc., with their receptors stimulates a wide variety of biological responses including, e.g., cell proliferation and differentiation, activation of mediating enzymes, stimulation of messenger turnover, alterations in ion fluxes, activation of enzymes, changes in cell shape and the alteration in genetic expression levels. Accordingly, control of the interaction of the receptor and its ligand may offer control of the biological responses caused by that interaction.

Accordingly, in one aspect, the present invention will be useful in screening for compounds that affect an interaction between a receptor molecule and its ligands. As used herein, the term "receptor" generally refers to one member of a pair of compounds which specifically recognize and bind to each other. The other member of the pair is termed a "ligand." Thus, a receptor/ligand pair may include a typical protein receptor, usually membrane associated, and its natural ligand, e.g., another protein or small molecule. Receptor/ligand pairs may also include antibody/antigen binding pairs, complementary nucleic acids, nucleic acid associating proteins and their nucleic acid ligands. A large number of specifically associating biochemical compounds are well known in the art and can be utilized in practicing the present invention.

Traditionally, methods for screening for effectors of a receptor/ligand interaction have involved incubating a receptor/ligand binding pair in the presence of a test compound. The level of binding of the receptor/ligand pair is then compared to negative and/or positive controls. Where a decrease in normal binding is seen, the test compound is determined to be an inhibitor of the receptor/ligand binding. Where an increase in that binding is seen, the test compound is determined to be an enhancer or inducer of the interaction.

In the interest of efficiency, screening assays have typically been set up in multiwell reaction plates, e.g., multiwell microplates, which allow for the simultaneous, parallel screening of large numbers of test compounds.

A similar, and perhaps overlapping, set of biochemical systems includes the interactions between enzymes and their substrates. The term "enzyme" as used herein, generally refers to a protein which acts as a catalyst to induce a chemical change in other compounds or "substrates."

Typically, effectors of an enzyme's activity toward its substrate are screened by contacting the enzyme with a substrate in the presence and absence of the compound to be screened and under conditions optimal for detecting changes in the enzyme's activity. After a set time for reaction, the mixture is assayed for the presence of reaction products or a decrease in the amount of substrate. The amount of substrate that has been catalyzed is them compared to a control, i.e., enzyme contacted with substrate in the absence of test compound or presence of a known effector. As above, a compound that reduces the enzymes activity toward its substrate is termed an "inhibitor," whereas a compound that accentuates that activity is termed an "inducer."

Generally, the various screening methods encompassed by the present invention involve the serial introduction of a plurality of test compounds into a microfluidic device. Once injected into the device, the test compound may be screened for effect on a biological system using a continuous serial or parallel assay orientation.

As used herein, the term "test compound" refers to the collection of compounds that are to be screened for their ability to affect a particular biochemical system. Test compounds may include a wide variety of different compounds, including chemical compounds, mixtures of chemical compounds, e.g., polysaccharides, small organic or inorganic molecules, biological macromolecules, e.g., peptides, proteins, nucleic acids, or an extract made from biological materials such as bacteria, plants, fungi, or animal cells or tissues, naturally occurring or synthetic compositions. Depending upon the particular embodiment being practiced, the test compounds may be provided, e.g., injected, free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, glass beads, polyaminemethylvinylether maleic acid copolymer, amino acid copolymer, ethylene-maleic acid copolymer, nylon, silk, etc. Additionally, for the methods and apparatuses described herein, test compounds may be screened individually, or in groups. Group screening is particularly useful where hit rates for effective test compounds are expected to be low such that one would not expect more than one positive result for a given group. Alternatively, such group screening may be used where the effects of different test compounds may be differentially detected in a single system, e.g., through electrophoretic separation of the effects, or differential labelling which enables separate detection.

II. Assay Systems

As described above, the screening methods of the present invention are generally carried out in microfluidic devices or "microlaboratory systems," which allow for integration of the elements required for performing the assay, automation, and minimal environmental effects on the assay system, e.g., evaporation, contamination, human error. A number of devices for carrying out the assay methods of the invention are described in substantial detail below. However, it will be recognized that the specific configuration of these devices will generally vary depending upon the type of assay and/or assay orientation desired. For example, in some embodiments, the screening methods of the invention can be carried out using a microfluidic device having two intersecting channels. For more complex assays or assay orientations, multichannel/intersection devices may be employed. The small scale, integratability and self-contained nature of these devices allows for virtually any assay orientation to be realized within the context of the microlaboratory system.

A. Continuous Flow Assay Systems

In one preferred aspect, the methods and apparatuses of the invention are used in screening test compounds using a continuous flow assay system. Generally, the continuous flow assay system can be readily used in screening for inhibitors or inducers of enzymatic activity, or for agonists or antagonists of receptor-ligand binding. In brief, the continuous flow assay system involves the continuous flow of the particular biochemical system along a microfabricated channel. As used herein, the term "continuous" generally refers to an unbroken or contiguous stream of the particular composition that is being continuously flowed. For example, a continuous flow may include a constant fluid flow having a set velocity, or alternatively, a fluid flow which includes pauses in the flow rate of the overall system, such that the pause does not otherwise interupt the flow stream. The functioning of the system is indicated by the production of a detectable event or signal. Typically, such detectable signals will include chromophoric or fluorescent signals that are associated with the functioning of the particular model system used. For enzyme systems, such signals will generally be produced by products of the enzyme's catalytic action, e.g., on a chromogenic or fluorogenic substrate. For binding systems, e.g., receptor ligand interactions, signals will typically involve the association of a labeled ligand with the receptor, or vice versa.

In preferred aspects, the continuous system generates a constant signal which varies only when a test compound is introduced that affects the system. Specifically, as the system components flow along the channel, they will produce a relatively constant signal level at a detection zone or window of the channel. Test compounds are periodically introduced into the channel and mixed with the system components. Where those test compounds have an effect on the system, it will cause a deviation from the constant signal level at the detection window. This deviation may then be correlated to the particular test compound screened.

One embodiment of a device for use in a serial or continuous assay geometry is shown in FIG. 1. As shown, the overall device 100 is fabricated in a planar substrate 102. Suitable substrate materials are generally selected based upon their compatibility with the conditions present in the particular operation to be performed by the device. Such conditions can include extremes of pH, temperature, salt concentration, and application of electrical fields. Additionally, substrate materials are also selected for their inertness to critical components of an analysis or synthesis to be carried out by the device.

Examples of useful substrate materials include, e.g., glass, quartz and silicon as well as polymeric substrates, e.g. plastics. In the case of conductive or semi-conductive substrates, it will generally be desirable to include an insulating layer on the substrate. This is particularly important where the device incorporates electrical elements, e.g., electrical fluid direction systems, sensors and the like. In the case of polymeric substrates, the substrate materials may be rigid, semi-rigid, or non-rigid, opaque, semi-opaque or transparent, depending upon the use for which they are intended. For example, devices which include an optical or visual detection element, will generally be fabricated, at least in part, from transparent materials to allow, or at least, facilitate that detection. Alternatively, transparent windows of, e.g., glass or quartz, may be incorporated into the device for these types detection elements. Additionally, the polymeric materials may have linear or branched backbones, and may be crosslinked or non-crosslinked. Examples of particularly preferred polymeric materials include, e.g., polydimethylsiloxanes (PDMS), polyurethane, polyvinylchloride (PVC) polystyrene, polysulfone, polycarbonate and the like.

The device shown in FIG. 1 includes a series of channels 110, 112, and optional reagent channel 114, fabricated into the surface of the substrate. At least one of these channels will typically have very small cross sectional dimensions, e.g., in the range of from about 0.1 $\mu$m to about 500 $\mu$m. Preferably the cross-sectional dimensions of the channels will be in the range of from about 0.1 to about 200 $\mu$m and more preferably in the range of from about 0.1 to about 100 $\mu$m. In particularly preferred aspects, each of the channels will have at least one cross-sectional dimension in the range of from about 0.1 $\mu$m to about 100 $\mu$m. Although generally shown as straight channels, it will be appreciated that in order to maximize the use of space on a substrate, serpentine, saw tooth or other channel geometries, to incorporate effectively longer channels in shorter distances.

Manufacturing of these microscale elements into the surface of the substrates may generally be carried out by any number of microfabrication techniques that are well known in the art. For example, lithographic techniques may be employed in fabricating, e.g., glass, quartz or silicon substrates, using methods well known in the semi-conductor manufacturing industries such as photolithographic etching, plasma etching or wet chemical etching. Alternatively, micromachining methods such as laser drilling, micromilling and the like may be employed. Similarly, for polymeric substrates, well known manufacturing techniques may also be used. These techniques include injection molding or stamp molding methods where large numbers of substrates may be produced using, e.g., rolling stamps to produce large sheets of microscale substrates or polymer microcasting techniques where the substrate is polymerized within a micromachined mold.

The devices will typically include an additional planar element which overlays the channeled substrate enclosing and fluidly sealing the various channels to form conduits. Attaching the planar cover element may be achieved by a variety of means, including, e.g., thermal bonding, adhesives or, in the case of certain substrates, e.g., glass, or semi-rigid and non-rigid polymeric substrates, a natural adhesion between the two components. The planar cover element may additionally be provided with access ports and/or reservoirs for introducing the various fluid elements needed for a particular screen.

The device shown in FIG. 1 also includes reservoirs 104, 106 and 108, disposed and fluidly connected at the ends of the channels 110 and 114. As shown, sample channel 112, is used to introduce the plurality of different test compounds into the device. As such, this channel will generally be fluidly connected to a source of large numbers of separate test compounds that will be individually introduced into the sample channel 112 and subsequently into channel 110.

The introduction of large numbers of individual, discrete volumes of test compounds into the sample may be carried out by a number of methods. For example, micropipettors may be used to introduce the test compounds into the device. In preferred aspects, an electropipettor may be used which is fluidly connected to sample channel 112. An example of such an electropipettor is described in, e.g., U.S. patent application Ser. No. 08/671,986, filed Jun. 28, 1996 (Attorney Docket No. 017646-000500) the disclosure of which is hereby incorporated herein by reference in its entirety for all purposes. Generally, this electropipettor utilizes electroosmotic fluid direction as described herein, to alternately sample a number of test compounds, or "subject materials," and spacer compounds. The pipettor then delivers individual, physically isolated sample or test compound volumes in subject material regions, in series, into the sample channel for subsequent manipulation within the device. Individual samples are typically separated by a spacer region of low ionic strength spacer fluid. These low ionic strength spacer regions have higher voltage drop over their length than do the higher ionic strength subject material or test compound regions, thereby driving the electrokinetic pumping. On either side of the test compound or subject material region, which is typically in higher ionic strength solution, are fluid regions referred to as first spacer regions (also referred to as "guard bands"), that contact the interface of the subject material regions. These first spacer regions typically comprise a high ionic strength solution to prevent migration of the sample elements into the lower ionic strength fluid regions, or second spacer region, which would result in electrophoretic bias. The use of such first and second spacer regions is described in greater detail in U.S. patent application Ser. No. 08/671,986, filed Jun. 28, 1996, (Attorney Docket No. 017646-000500) which is incorporated herein by reference.

Alternatively, the sample channel 112 may be individually fluidly connected to a plurality of separate reservoirs via separate channels. The separate reservoirs each contain a separate test compound with additional reservoirs being provided for appropriate spacer compounds. The test compounds and/or spacer compounds are then transported from the various reservoirs into the sample channels using appropriate fluid direction schemes. In either case, it generally is desirable to separate the discrete sample volumes, or test compounds, with appropriate spacer regions.

As shown, the device also includes a detection window or zone 116 at which a signal from the biochemical system may be monitored. This detection window typically will include a transparent cover allowing visual or optical observation and detection of the assay results, e.g., observation of a colorometric or fluorometric response.

In particularly preferred aspects, monitoring of the signals at the detection window is achieved using an optical detection system. For example, fluorescence based signals are typically monitored using, e.g., laser activated fluorescence detection systems which employ a laser light source at an appropriate wavelength for activating the fluorescent indicator within the system. Fluorescence is then detected using an appropriate detector element, e.g., a photomultiplier tube (PMT). Similarly, for screens employing colorometric signals, spectrophotometric detection systems may be employed which direct a light source at the sample and provide a measurement of absorbance or transmissivity of the sample.

In alternative aspects, the detection system may comprise a non-optical detectors or sensors for detecting a particular characteristic of the system disposed within detection window 116. Such sensors may include temperature, conductivity, potentiometric (pH, ions), amperometric (for compounds that may be oxidized or reduced, e.g., $O_2$, $H_2O_2$, $I_2$, oidzable/reducible organic compounds, and the like).

In operation, a fluid first component of a biological system, e.g., a receptor or enzyme, is placed in reservoir 104.

This first component is flowed through main channel 110, past the detection window, 116, and toward waste reservoir 108. A second component of the biochemical system, e.g., a ligand or substrate, is concurrently flowed into the main channel 110 from the side channel 114, whereupon the first and second components mix and are able to interact. Deposition of these elements within the device may be carried out in a number of ways. For example, the enzyme and substrate, or receptor and ligand solutions can be introduced into the device through open or sealable access ports in the planar cover. Alternatively, these components may be added to their respective reservoirs during manufacture of the device. In the case of such pre-added components, it may be desirable to provide these components in a stabilized form to allow for prolonged shelf-life of the device. For example, the enzyme/substrate or receptor/ligand components may be provided within the device in lyophilized form. Prior to use, these components may be easily reconstituted by introducing a buffer solution into the reservoirs. Alternatively, the components may be lyophilized with appropriate buffering salts, whereby simple water addition is all that is required for reconstitution.

As noted above, the interaction of the first and second components is typically accompanied by a detectable signal. For example, in those embodiments where the first component is an enzyme and the second a substrate, the substrate may be a chromogenic or fluorogenic substrate which produces an optically detectable signal when the enzyme acts upon the substrate. In the case where the first component is a receptor and the second is a ligand, either the ligand or the receptor may bear a detectable signal. In either event, the mixture and flow rate of compounds will typically remain constant such that the flow of the mixture of the first and second components past the detection window 116 will produce a steady-state signal. By "steady state signal" is generally meant a signal that has a regular, predictable signal intensity profile. As such, the steady-state signal may include signals having a constant signal intensity, or alternatively, a signal with a regular periodic intensity, against which variations in the normal signal profile may be measured. This latter signal may be generated in cases where fluid flow is periodically interrupted for, e.g., loading additional test compounds, as described in the description of the continuous flow systems. Although the signal produced in the above-described enzymatic system will vary along the length of the channel, i.e., increasing with time of exposure as the enzyme converts the fluorogenic substrate to the fluorescent product, the signal at any specific point along the channel will remain constant, given a constant flow rate.

From sample channel 112, test compounds may be periodically or serially introduced into the main channel 110 and into the stream of first and second components as fluid regions containing the test compound, also referred to as the "subject material regions." Where these test compounds have an effect on the interaction of the first and second elements, it will produce a deviation in the signal detected at the detection window corresponding to the subject material region. As noted above, typically, the various different test compounds to be injected through channel 112 will be separated by a first and even second spacer fluid regions to allow differentiation of the effects, or lack of effects, from one test compound to another. In those embodiments where electroosmotic fluid direction systems are employed, the spacer fluid regions may also function to reduce any electrophoretic bias that can occur within the test sample. The use of these spacer regions to drive the electroosmotic flow of fluids, as well as in the general elimination of electrophoretic bias within the sample or test compound or subject material regions is substantially described in U.S. patent application Ser. No. 08/671,986, filed Jun. 28, 1996 (Attorney Docket No. 017646-000500), previously incorporated herein by reference.

By way of example, a steady, continuous flow of enzyme and fluorogenic substrate through main channel 110 will produce a constant fluorescent signal at the detection window 116. Where a test compound inhibits the enzyme, introduction of a test compound, i.e., in a subject material region, will produce a momentary but detectable drop in the level of signal at the detection window corresponding with that subject material region. The timing of the drop in signal can then be correlated with a particular test compound based upon a known injection to detection time-frame. Specifically, the time required for an injected compound to produce an observed effect can be readily determined using positive controls.

For receptor/ligand systems, a similar variation in the steady state signal may also be observed. Specifically, the receptor and its fluorescent ligand can be made to have different flow rates along the channel. This can be accomplished by incorporating size exclusion matrices within the channel, or, in the case of electroosmotic methods, altering the relative electrophoretic mobility of the two compounds so that the receptor flows more rapidly down the channel. Again, this may be accomplished through the use of size exclusion matrices, or through the use of different surface charges in the channel which will result in differential flow rates of charge-varied compounds. Where a test compound binds to the receptor, it will result in a dark pulse in the fluorescent signal followed by a brighter pulse. Without being bound to a particular theory of operation, it is believed that the steady state signal is a result of both free fluorescent ligand, and fluorescent ligand bound to the receptor. The bound ligand is traveling at the same flow rate as the receptor while the unbound ligand is traveling more slowly. Where the test compound inhibits the receptor-ligand interaction, the receptor will not 'bring along' the fluorescent ligand, thereby diluting the fluorescent ligand in the direction of flow, and leaving an excess of free fluorescent ligand behind. This results in a temporary reduction in the steady-state signal, followed by a temporary increase in fluorescence. Alternatively, schemes similar to those employed for the enzymatic system may be employed, where there is a signal that reflects the interaction of the receptor with its ligand. For example, pH indicators which indicate pH effects of receptor-ligand binding may be incorporated into the device along with the biochemical system, i.e., in the form of encapsulated cells, whereby slight pH changes resulting from binding can be detected. See Weaver, et al., *Bio/Technology* (1988) 6:1084–1089. Additionally, one can monitor activation of enzymes resulting from receptor ligand binding, e.g., activation of kinases, or detect conformational changes in such enzymes upon activation, e.g., through incorporation of a fluorophore which is actuivated or quenched by the conformational change to the enzyme upon activation.

Flowing and direction of fluids within the microscale fluidic devices may be carried out by a variety of methods. For example, the devices may include integrated microfluidic structures, such as micropumps and microvalves, or external elements, e.g., pumps and switching valves, for the pumping and direction of the various fluids through the device. Examples of microfluidic structures are described in, e.g., U.S. Pat. Nos. 5,271,724, 5,277,556, 5,171,132, and 5,375,979. See also, Published U.K. Patent Application No. 2 248 891 and Published European Patent Application No. 568 902.

Although microfabricated fluid pumping and valving systems may be readily employed in the devices of the invention, the cost and complexity associated with their manufacture and operation can generally prohibit their use in mass-produced disposable devices as are envisioned by the present invention. For that reason, in particularly preferred aspects, the devices of the invention will typically include an electroosmotic fluid direction system. Such fluid direction systems combine the elegance of a fluid direction system devoid of moving parts, with an ease of manufacturing, fluid control and disposability. Examples of particularly preferred electroosmotic fluid direction systems include, e.g., those described in International Patent Application No. WO 96/04547 to Ramsey et al., which is incorporated herein by reference in its entirety for all purposes.

In brief, these fluidic control systems typically include electrodes disposed within the reservoirs that are placed in fluid connection with the plurality of intersecting channels fabricated into the surface of the substrate. The materials stored in the reservoirs are transported through the channel system delivering appropriate volumes of the various materials to one or more regions on the substrate in order to carry out a desired screening assay.

Fluid transport and direction is accomplished through electroosmosis or electrokinesis. In brief, when an appropriate fluid is placed in a channel or other fluid conduit having functional groups present at the surface, those groups can ionize. For example, where the surface of the channel includes hydroxyl functional groups at the surface, protons can leave the surface of the channel and enter the fluid. Under such conditions, the surface will possess a net negative charge, whereas the fluid will possess an excess of protons or positive charge, particularly localized near the interface between the channel surface and the fluid. By applying an electric field along the length of the channel, cations will flow toward the negative electrode. Movement of the positively charged species in the fluid pulls the solvent with them. The steady state velocity of this fluid movement is generally given by the equation:

$$v = \frac{\epsilon \xi E}{4\pi \eta}$$

where v is the solvent velocity, $\epsilon$ is the dielectric constant of the fluid, $\xi$ is the zeta potential of the surface, E is the electric field strength, and $\eta$ is the solvent viscosity. Thus, as can be easily seen from this equation, the solvent velocity is directly proportional to the surface potential.

To provide appropriate electric fields, the system generally includes a voltage controller that is capable of applying selectable voltage levels, simultaneously, to each of the reservoirs, including ground. Such a voltage controller can be implemented using multiple voltage dividers and multiple relays to obtain the selectable voltage levels. Alternatively, multiple, independent voltage sources may be used. The voltage controller is electrically connected to each of the reservoirs via an electrode positioned or fabricated within each of the plurality of reservoirs.

Incorporating this electroosmotic fluid direction system into the device shown in FIG. 1 involves incorporation of an electrode within each of the reservoirs 104, 106 and 108, and at the terminus of sample channel 112 or at the terminus of any fluid channels connected thereto, whereby the electrode is in electrical contact with the fluid disposed in the respective reservoir or channel. Substrate materials are also selected to produce channels having a desired surface charge. In the case of glass substrates, the etched channels will possess a net negative charge resulting from the ionized hydroxyls naturally present at the surface. Alternatively, surface modifications may be employed to provide an appropriate surface charge, e.g., coatings, derivatization, e.g., silanation, or impregnation of the surface to provide appropriately charged groups on the surface. Examples of such treatments are described in, e.g., Provisional Patent Application Ser. No. 60/015,498, filed Apr. 16, 1996 (Attorney Docket No. 017646-002600) which is hereby incorporated herein by reference in its entirety for all purposes.

Modulating voltages are then concomitantly applied to the various reservoirs to affect a desired fluid flow characteristic, e.g., continuous flow of receptor/enzyme, ligand/substrate toward the waste reservoir with the periodic introduction of test compounds. Particularly, modulation of the voltages applied at the various reservoirs can move and direct fluid flow through the interconnected channel structure of the device in a controlled manner to effect the fluid flow for the desired screeening assay and apparatus.

Figure 2A:
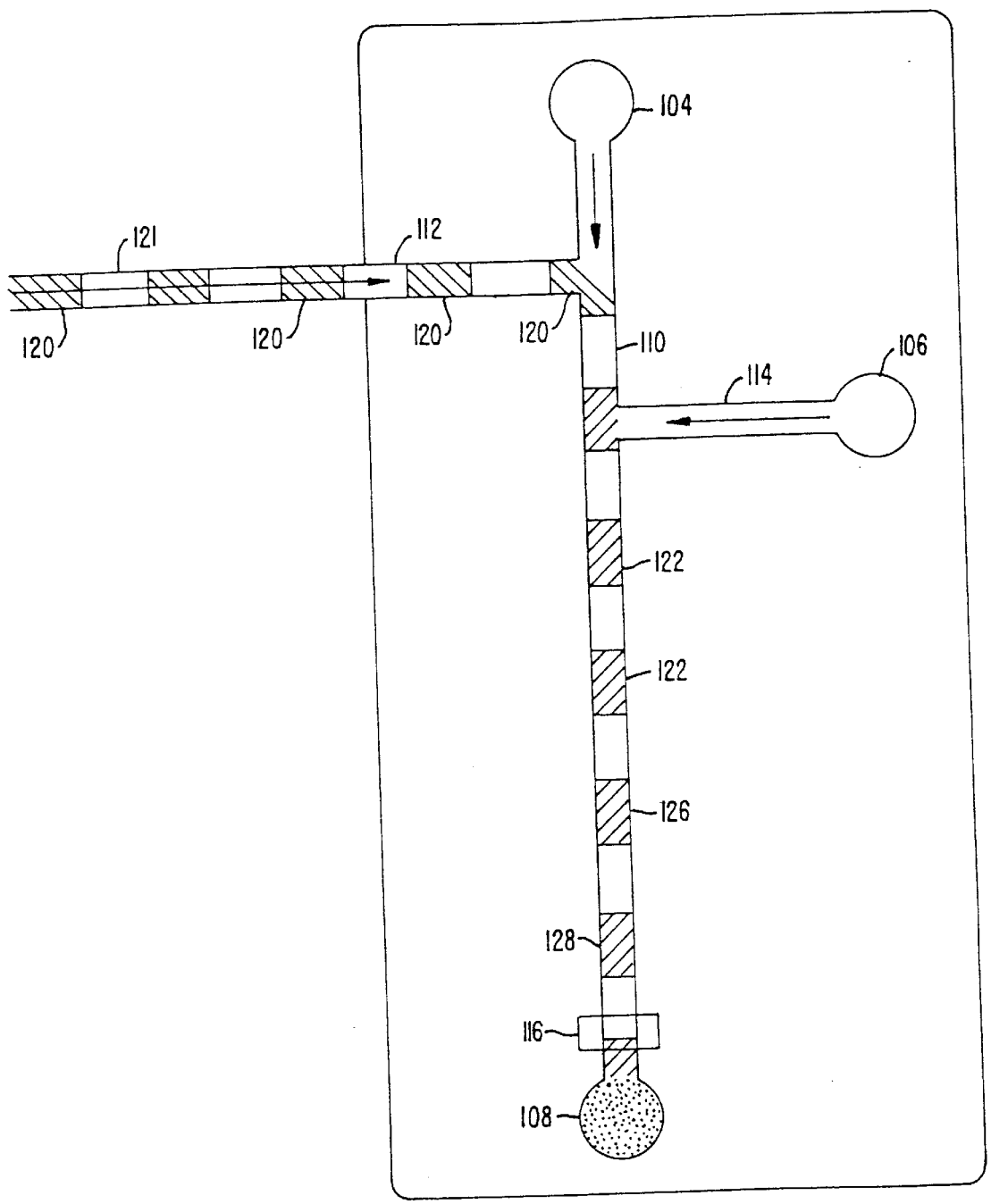
FIGS. 2A and 2B show a schematic illustration of the apparatus shown in FIG. 1, operating in alternate assay systems.

FIG. 2A shows a schematic illustration of fluid direction during a typical assay screen. Specifically, shown is the injection of a test compound (in a subject material region) into a continuous stream of an enzyme-fluorogenic substrate mixture. As shown in FIG. 2A, and with reference to FIG. 1, a continuous stream of enzyme is flowed from reservoir 104, along main channel 110. Test compounds 120, separated by appropriate spacer regions 121, e.g., low ionic strength spacer regions, are introduced from sample channel 112 into main channel 110. Once introduced into the main channel, the test compounds will interact with the flowing enzyme stream. The mixed enzyme/test compound regions are then flowed along main channel 110 past the intersection with channel 114. A continuous stream of fluorogenic or chromogenic substrate which is contained in reservoir 106, is introduced into sample channel 110, whereupon it contacts and mixes with the continuous stream of enzyme, including the subject material regions which include the test compounds 122. Action of the enzyme upon the substrate will produce an increasing level of the fluorescent or chromatic signal. This increasing signal is indicated by the increasing shading within the main channel as it approaches the detection window. This signal trend will also occur within those test compound or subject material regions which have no effect on the enzyme/substrate interaction, e.g., test compound 126. Where a test compound does have an effect on the interaction of the enzyme and the substrate, a variation will appear in the signal produced. For example, assuming a fluorogenic substrate, a test compound which inhibits the interaction of the enzyme with its substrate will result in less fluorescent product being produced within that subject material region. This will result in a non-fluorescent, or detectably less fluorescent region within the flowing stream as it passes detection window 116, which corresponds to the subject material region. For example, as shown, a subject material region including a test compound 128, which is a putative inhibitor of the enzyme-substrate interaction, shows detectably lower flourescence than the surrounding stream. This is indicated by a lack of shading of subject material region 128.

A detector adjacent to the detection window monitors the level of fluorescent signal being produced by the enzyme's activity on the fluorogenic or chromogenic substrate. This signal remains at a relatively constant level for those test compounds which have no effect on the enzyme-substrate interaction. When an inhibitory compound is screened, however, it will produce a momentary drop in the fluorescent signal representing the reduced or inhibited enzyme activity toward the substrate. Conversely, inducer compounds upon screening, will produce a momentary increase in the fluorescent signal, corresponding to the increased enzyme activity toward the substrate.

Figure 2B:
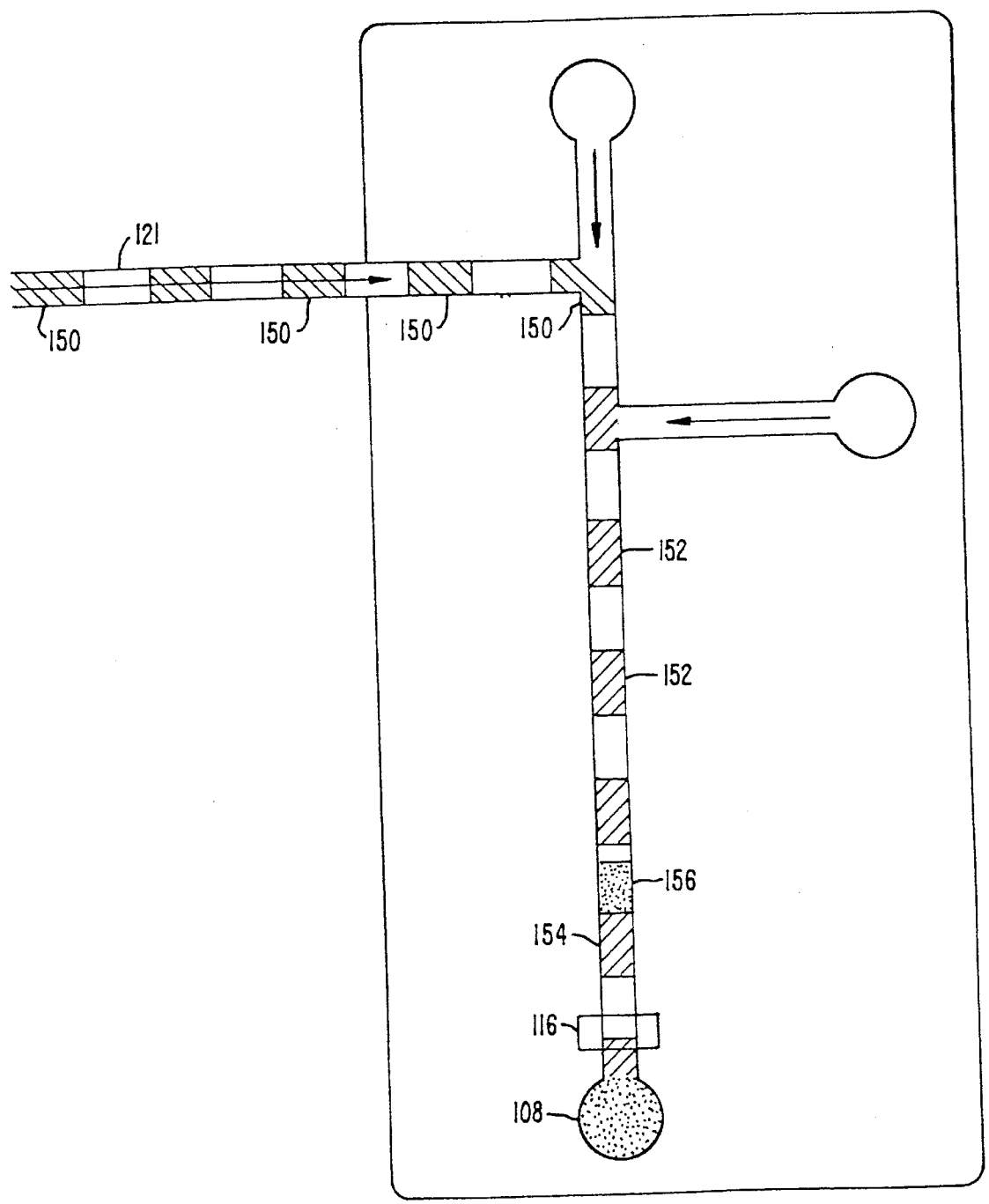

FIG. 2B provides a similar schematic illustration of a screen for effectors of a receptor-ligand interaction. As in FIG. 2A, a continuous stream of receptor is flowed from reservoir 104 through main channel 110. Test compounds or subject material regions 150 separated by appropriate spacer fluid regions 121 are introduced into the main channel 110 from sample channel 112, and a continuous stream of fluorescent ligand from reservoir 106 is introduced from side channel 114. Fluorescence is indicated by shading within the channel. As in FIG. 2A, the continuous stream of fluorescent ligand and receptor past the detection window 116 will provide a constant signal intensity. The subject material regions in the stream, containing the test compounds which have no effect on the receptor-ligand interaction, will provide the same or similar level of fluorescence as the rest of the surrounding stream, e.g., test compound or subject material region 152. However, the presence of test compounds which possess antagonistic or inhibitory activity toward the receptor-ligand interaction will result in lower levels of that interaction in those portions of the stream where those compounds are located, e.g., test compound or subject material region 154. Further, differential flow rates for the receptor bound fluorescent ligand and free fluorescent ligand will result in a detectable drop in the level of fluorescence which corresponds to the dilution of the fluorescence resulting from unbound, faster moving receptor. The drop in fluorescence is then followed by an increase in fluorescence 156 which corresponds to an accumulation of the slower moving, unbound fluorescent ligand.

In some embodiments, it may be desirable to provide an additional channel for shunting off or extracting the subject material region reaction mixture from the running buffer and/or spacer regions. This may be the case where one wishes to keep the reaction elements contained within the a discrete fluid region during the reaction, while allowing these elements to be separated during a data acquisition stage. As described previously, one can keep the various elements of the reaction together in the subject material region that is moving through the reaction channel by incorporating appropriate spacer fluid regions between samples. Such spacer fluid regions are generally selected to retain the samples within their original subject material regions, i.e., not allowing smearing of the sample into the spacer regions, even during prolonged reaction periods. However, this goal can be at odds with those assays which are based upon the separation of elements of the assay, e.g., ligand-receptor assays described above, or where a reaction product must be separated in a capillary. Thus, it may be desirable to remove those elements which prevented such separation during the initial portions of the fluid direction.

Figure 5:
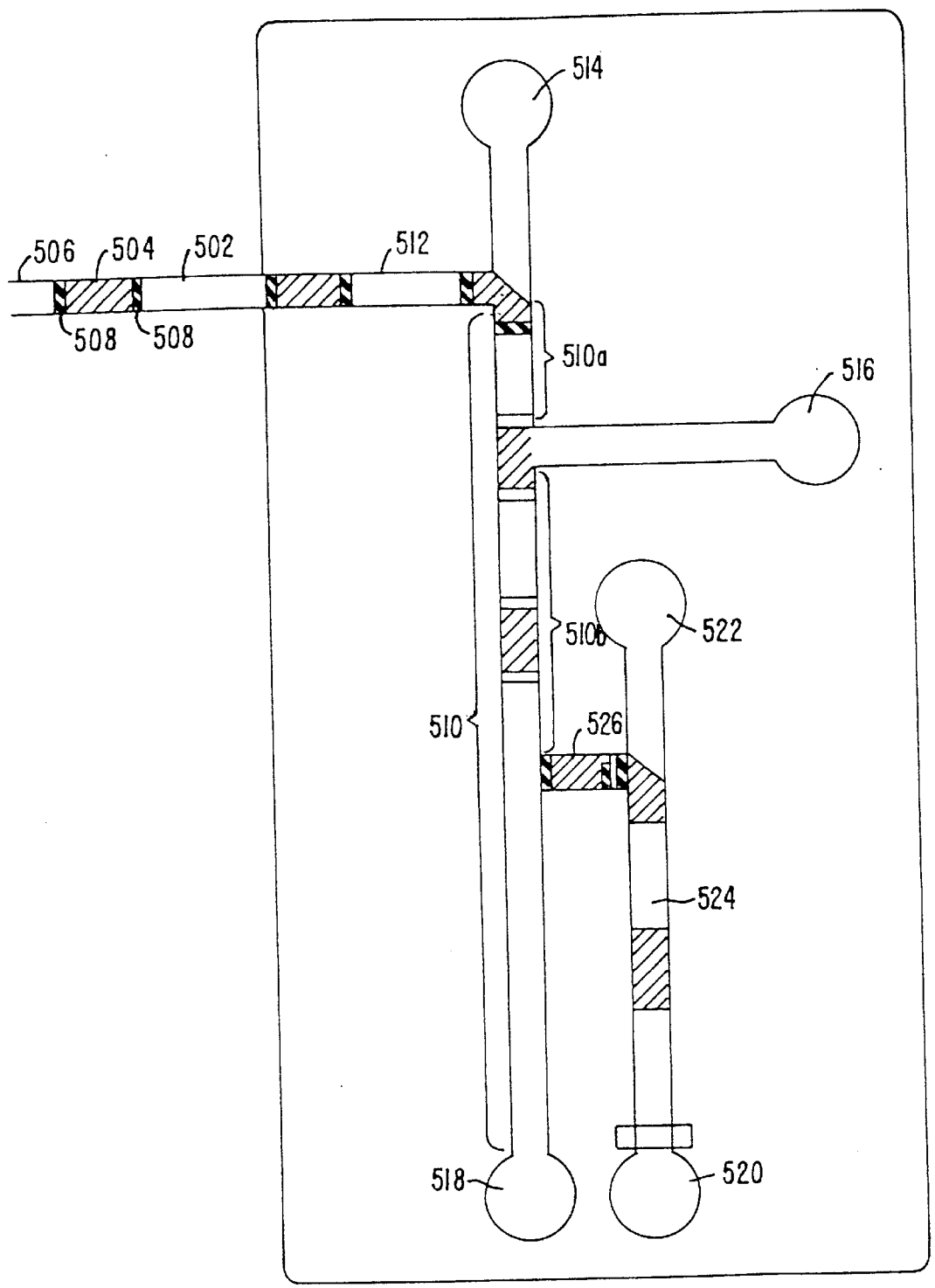
FIG. 5 shows a schematic illustration of a continuous flow assay device incorporating a sample shunt for performing prolonged incubation followed by a separation step.

A schematic illustration of one embodiment of a device 500 for performing this sample or subject material shunting or extraction is shown in FIG. 5. As shown, the subject materials or test compounds 504 are introduced to the device or chip via the sample channel 512. Again, these are typically introduced via an appropriate injection device 506, e.g., a capillary pipettor. The ionic strength and lengths of the first spacer regions 508 and second spacer regions 502 are selected such that those samples with the highest electrophoretic mobility will not migrate through the first spacer regions 508 into the second spacer regions 502 in the length of time that it takes the sample to travel down the reaction channel.

Assuming a receptor ligand assay system, test compounds pass into the device 500 and into reaction channel 510, where they are first combined with the receptor. The test compound/receptor, in the form of the subject material regions, are flowed along the reaction channel in the incubation zone 510a. Following this initial incubation, the test compound/receptor mix is combined with a labelled ligand (e.g., fluorescent ligand) whereupon this mixture flows along the second incubation region 510b of reaction channel 510. The lengths of the incubation regions and the flow rates of the system (determined by the potentials applied at each of the reservoirs 514, 516, 518, 520, 522, and at the terminus of sample channel 512) determine the time of incubation of the receptor with the fluorescent ligand and test compound. The ionic strengths of the solutions containing the receptors and fluorescent ligands, as well as the flow rates of material from the reservoirs housing these elements into the sample channel are selected so as to not interfere with the first and second spacer regions.

The isolated sample plugs or subject material regions containing receptor, fluorescent ligand and test compound are flowed along the reaction channel 510 by the application of potentials at, e.g., reservoirs 514, 516, 518 and at the terminus of sample channel 512. Potentials are also applied at reservoirs 520 and 522, at the opposite ends of separation channel 524, to match the potentials at the two ends of the transfer channel, so that the net flow across the transfer channel is zero. As the subject material region passes the intersection of reaction channel 510 and transfer channel 526, the potentials are allowed to float at reservoirs 518 and 522, whereupon the potentials applied at reservoirs 514, 516, 520, and at the terminus of sample channel 512, result in the subject material region being shunted through transfer channel 526 and into separation channel 524. Once in the separation channel, the original potentials are reapplied to all of the reservoirs to stop the net fluid flow through transfer channel 526. The diversion of the subject material can then be repeated with each subsequent subject material region. Within the separation channel, the subject material region may be exposed to different conditions than those of the reaction channel. For example, a different flow rate may be used, capillary treatments may allow for separation of differentially charged or different sized species, and the like. In a preferred aspect, the subject material is shunted into the separation channel to place the subject material into a capillary filled with high ionic strength buffer, i.e., to remove the low ionic strength spacer regions, thereby allowing separation of the various sample components outside the confines of the original subject material region. For example, in the case of the above-described receptor/ligand screen, the receptor/ligand complex may have a different electrophoretic mobility from the ligand alone, in the transfer channel, thereby allowing more pronounced separation of the complex from the ligand, and its subsequent detection.

Such modifications have a wide variety of uses, particularly where it may be desirable to separate reaction products following reaction, e.g., in cleavage reactions, fragmentation reactions, PCR reactions, and the like.

B. Serial in Parallel Assay Systems

Figure 3:
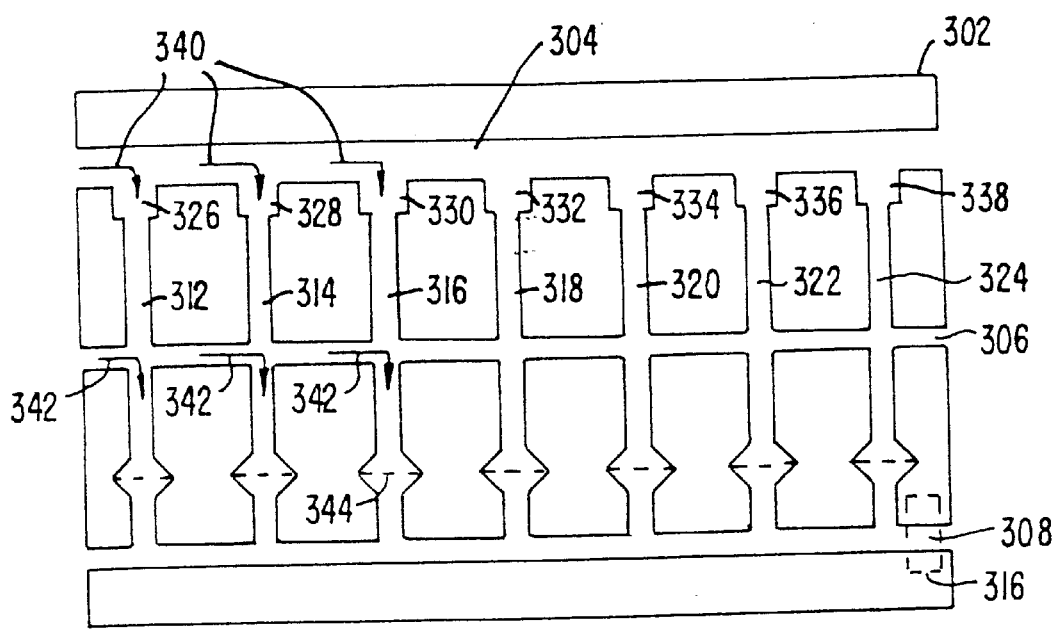
FIG. 3 is a schematic illustration of a "serial input parallel reaction" microlaboratory assay system in which compounds to be screened are serially introduced into the device but then screened in a parallel orientation within the device.

More complex systems can also be produced within the scope of the present invention. For example, a schematic illustration of one alternate embodiment employing a "serial input parallel reaction" geometry is shown in FIG. 3. As shown, the device 300 again includes a planar substrate 302 as described previously. Fabricated into the surface of the substrate 302 are a series of parallel reaction channels 312–324. Also shown are three transverse channels fluidly connected to each of these parallel reaction channels. The three transverse channels include a sample injection channel 304, an optional seeding channel 306 and a collection channel 308. Again, the substrate and channels are generally fabricated utilizing the materials and to the dimensions generally described above. Although shown and described in terms of a series of parallel channels, the reaction channels may also be fabricated in a variety of different orientations. For example, rather than providing a series of parallel channels fluidly connected to a single transverse channel, the channels may be fabricated connecting to and extending radially outward from a central reservoir, or may be arranged in some other non-parallel fashion. Additionally, although shown with three transverse channels, it will be recognized that fewer transverse channels may be used where, e.g., the biochemical system components are predisposed within the device. Similarly, where desired, more transverse channels may be used to introduce further elements into a given assay screen. Accordingly, the serial-in-parallel devices of the present invention will typically include at least two and preferably three, four, five or more transverse channels. Similarly, although shown with 7 reaction channels, it will be readily appreciated that the microscale devices of the present invention will be capable of comprising more than 7 channels, depending upon the needs of the particular screen. In preferred aspects, the devices will include from 10 to about 500 reaction channels, and more preferably, from 20 to about 200 reaction channels.

This device may be particularly useful for screening test compounds serially injected into the device, but employing a parallel assay geometry, once the samples are introduced into the device, to allow for increased throughput.

In operation, test compounds in discrete subject material regions, are serially introduced into the device, separated as described above, and flowed along the transverse sample injection channel 304 until the separate subject material regions are adjacent the intersection of the sample channel 304 with the parallel reaction channels 310–324. As shown in FIGS. 4A–4F, the test compounds may be provided immobilized on individual beads. In those cases where the test compounds are immobilized on beads, the parallel channels may be optionally fabricated to include bead resting wells 326–338 at the intersection of the reaction channels with the sample injection channel 304. Arrows 340 indicate the net fluid flow during this type of sample/bead injection. As individual beads settle into a resting well, fluid flow through that particular channel will be generally restricted. The next bead in the series following the unrestricted fluid flow, then flows to the next available resting well to settle in place.

Once in position adjacent to the intersection of the parallel reaction channel and the sample injection channel, the test compound is directed into its respective reaction channel by redirecting fluid flows down those channels. Again, in those instances where the test compound is immobilized on a bead, the immobilization will typically be via a cleavable linker group, e.g., a photolabile, acid or base labile linker group. Accordingly, the test compound will typically need to be released from the bead, e.g., by exposure to a releasing agent such as light, acid, base or the like prior to flowing the test compound down the reaction channel.

Within the parallel channel, the test compound will be contacted with the biochemical system for which an effector compound is being sought. As shown, the first component of the biochemical system is placed into the reaction channels using a similar technique to that described for the test compounds. In particular, the biochemical system is typically introduced via one or more transverse seeding channels 306. Arrows 342 illustrate the direction of fluid flow within the seeding channel 306. The biochemical system may be solution based, e.g., a continuously flowing enzyme/substrate or receptor-ligand mixture, like that described above, or as shown in FIGS. 4A–4F, may be a whole cell or bead based system, e.g., beads which have enzyme/substrate systems immobilized thereon.

In those instances where the biochemical system is incorporated in a particle, e.g., a cell or bead, the parallel channel may include a particle retention zone 344. Typically, such retention zones will include a particle sieving or filtration matrix, e.g., a porous gel or microstructure which retains particulate material but allows the free flow of fluids. Examples of microstructures for this filtration include, e.g., those described in U.S. Pat. No. 5,304,487, which is hereby incorporated by reference in its entirety for all purposes. As with the continuous system, fluid direction within the more complex systems may be generally controlled using microfabricated fluid direction structures, e.g., pumps and valves. However, as the systems grow more complex, such systems become largely unmanageable. Accordingly, electroosmotic systems, as described above, are generally preferred for controlling fluid in these more complex systems. Typically, such systems will incorporate electrodes within reservoirs disposed at the termini of the various transverse channels to control fluid flow thorough the device. In some aspects, it may be desirable to include electrodes at the termini of all the various channels. This generally provides for more direct control, but also grows less managable as systems grow more complex. In order to utilize fewer electrodes and thus reduce the potential complexity, it may often be desireable in parallel systems, e.g., where two fluids are desired to move at similar rates in parallel channels, to adjust the geometries of the various flow channels. In particular, as channel length increases, resistance along that channel will also increase. As such, flow lengths between electrodes should be designed to be substantially the same regardless of the parallel path chosen. This will generally prevent the generation of transverse electrical fields and thus promote equal flow in all parallel channels. To accomplish substantially the same resistance between the electrodes, one can alter the geometry of the channel structure to provide for the same channel length, and thus, the channel resistance, regardless of the path travelled. Alternatively, resistance of channels may be adjusted by varying the cross-sectional dimensions of the paths, thereby creating uniform resistance levels regardless of the path taken.

As the test compounds are drawn through their respective parallel reaction channels, they will contact the biochemical system in question. As described above, the particular biochemical system will typically include a flowable indicator system which indicates the relative functioning of that system, e.g., a soluble indicator such as chromogenic or fluorogenic substrate, labelled ligand, or the like, or a particle based signal, such as a precipitate or bead bound signalling group. The flowable indicator is then flowed through the respective parallel channel and into the collection channel 308 whereupon the signals from each of the parallel channels are flowed, in series, past the detection window, 116.

FIGS. 4A–4F, with reference to FIG. 3, show a schematic illustration of the progression of the injection of test compounds and biochemical system components into the "serial input parallel reaction" device, exposure of the system to the test compounds, and flowing of the resulting signal out of the parallel reaction channels and past the detection window.

Figure 4A:
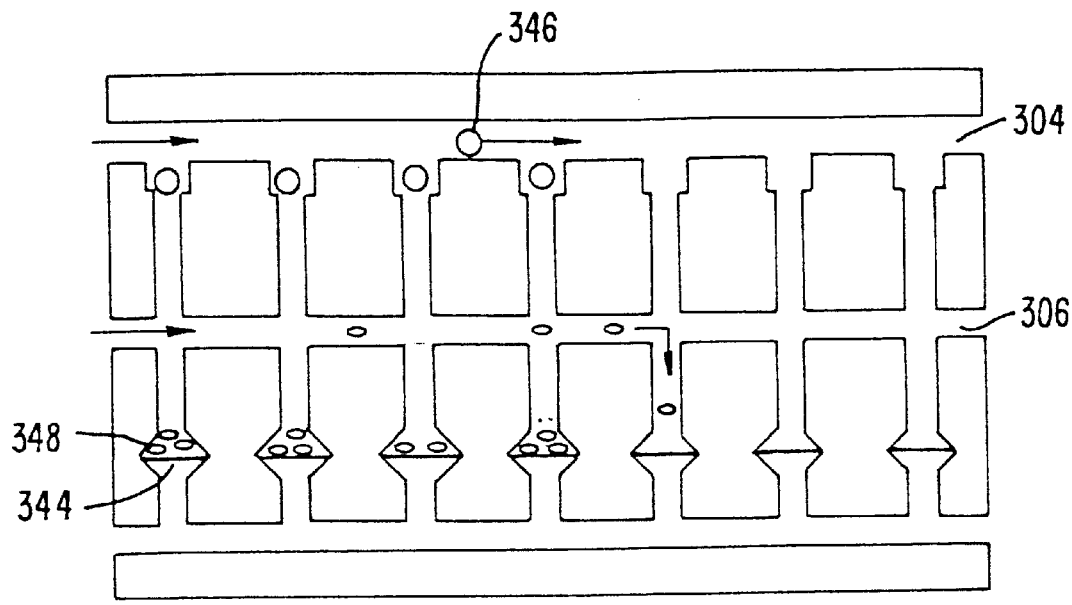
FIGS. 4A–4F show a schematic illustration of the operation of the device shown in FIG. 3, in screening a plurality of bead based test compounds.

In particular, FIG. 4A shows the introduction of test compounds immobilized on beads 346 through sample injection channel 304. Similarly, the biochemical system components 348 are introduced into the reaction channels 312–324 through seeding channel 306.

Although shown as being introduced into the device along with the test compounds, as described above, the components of the model system to be screened may be incorporated into the reaction channels during manufacture. Again, such components may be provided in liquid form or in lyophilized form for increased shelf life of the particular screening device.

As shown, the biochemical system components are embodied in a cellular or particle based system, however, fluid components may also be used as described herein. As the particulate components flow into the reaction channels, they may be retained upon an optional particle retaining matrix 344, as described above.

Figure 4B:
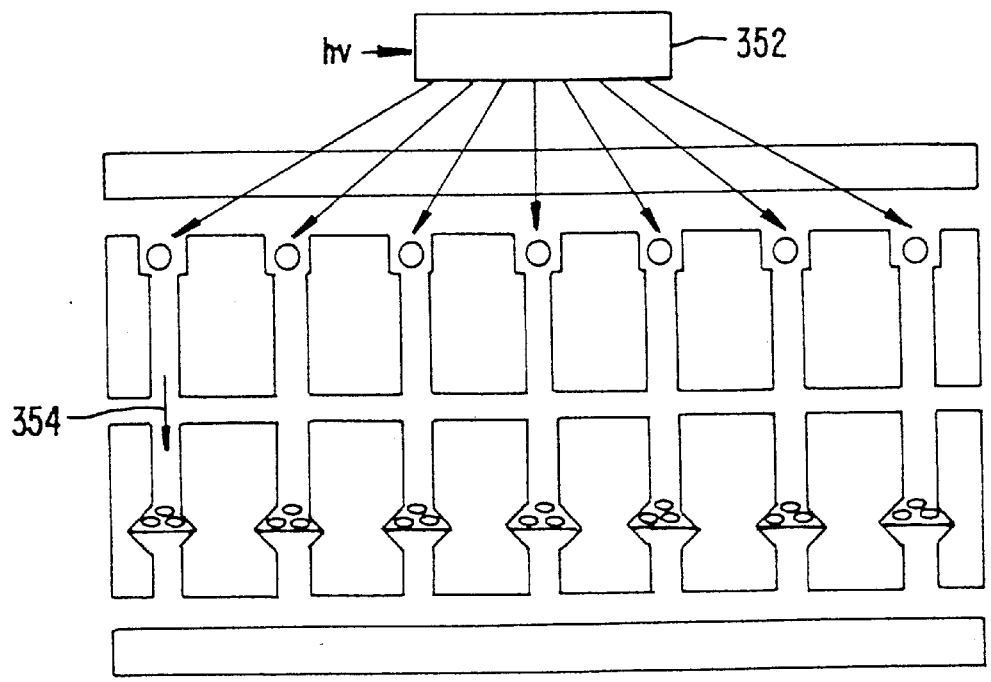

FIG. 4B illustrates the release of test compounds from the beads 346 by exposing the beads to a releasing agent. As shown, the beads are exposed to light from an appropriate light source 352, e.g., which is able to produce light in a wavelength sufficient to photolyze the linker group, thereby releasing compounds that are coupled to their respective beads via a photolabile linker group.

Figure 4C:
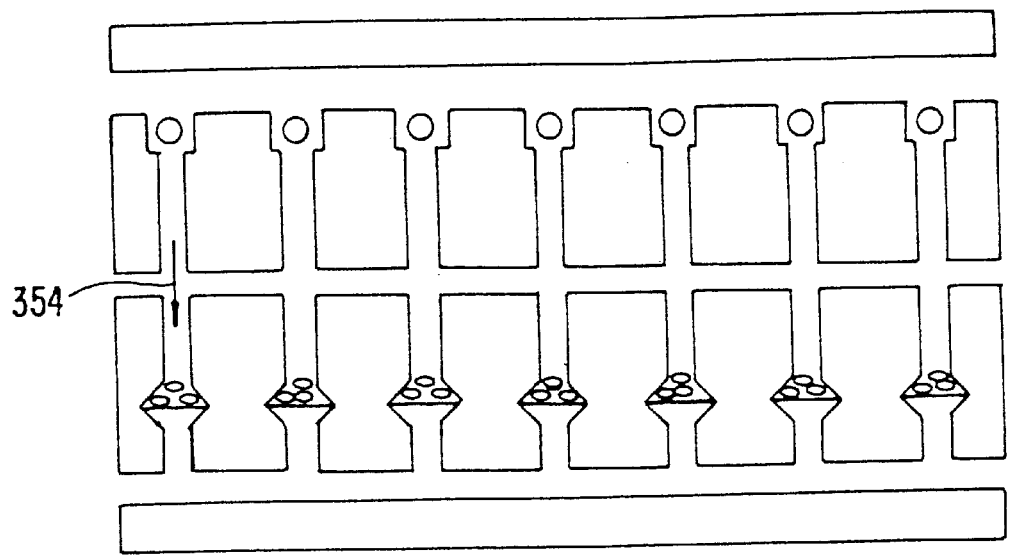
Figure 4D:
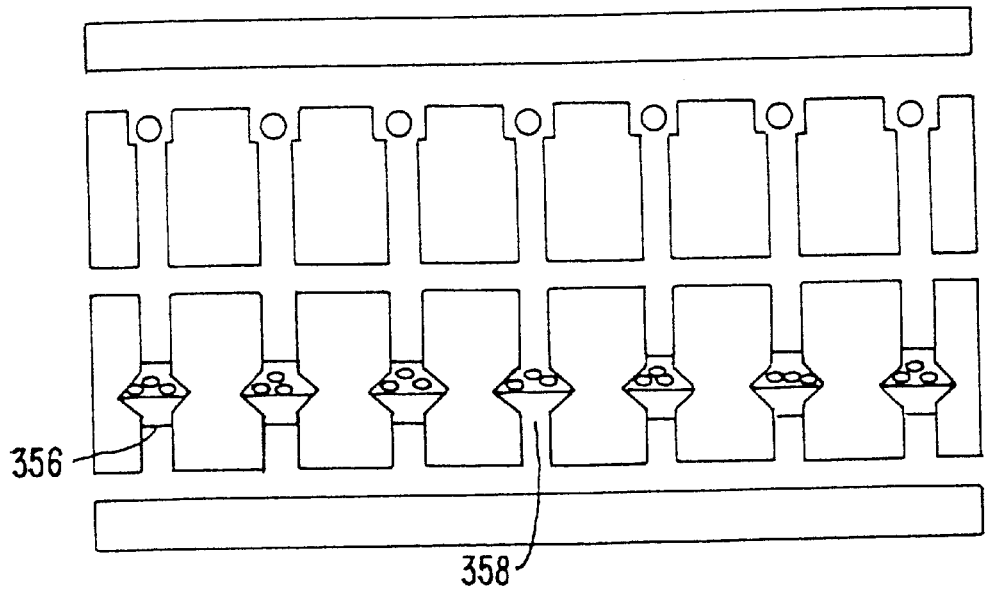

In FIG. 4C, the released test compounds are flowed into and along the parallel reaction channels as shown by arrows 354 until they contact the biochemical system components. The biochemical system components 348 are then allowed to perform their function, e.g., enzymatic reaction, receptor/ligand interaction, and the like, in the presence of the test compounds. Where the various components of the biochemical system are immobilized on a solid support, release of the components from their supports can provide the initiating event for the system. A soluble signal 356 which corresponds to the functioning of the biochemical system is then generated (FIG. 4D). As described previously, a variation in the level of signal produced is an indication that the particular test compound is an effector of the particular biochemical system. This is illustrated by the lighter shading of signal 358.

Figure 4E:
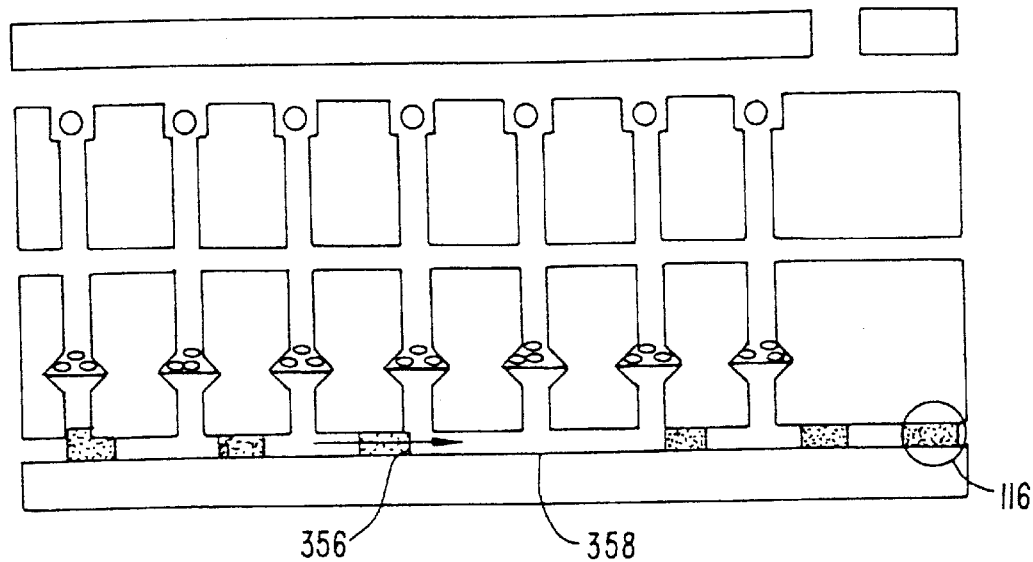
Figure 4F:
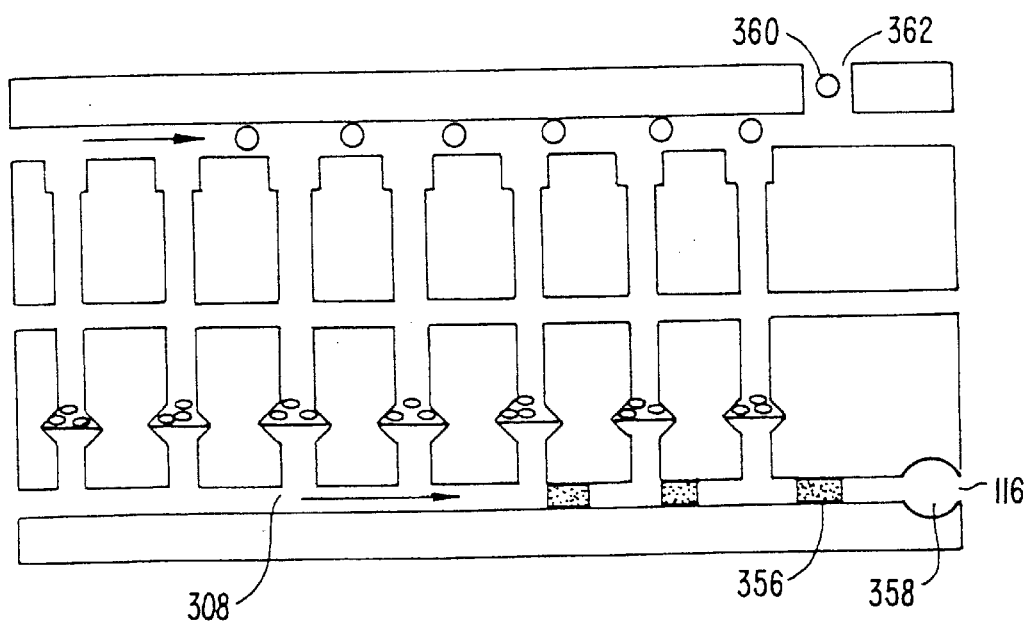

In FIGS. 4E and 4F, the soluble signal is then flowed out of reactions channels 312–324 into the detection channel 308, and along the detection channel past the detection window 116.

Again, a detection system as described above, located adjacent the detection window will monitor the signal levels. In some embodiments, the beads which bore the test compounds may be recovered to identify the test compounds which were present thereon. This is typically accomplished by incorporation of a tagging group during the synthesis of the test compound on the bead. As shown, spent bead 360, i.e., from which a test compound has been released, may be transported out of the channel structure through port 362 for identification of the test compound that had been coupled to it. Such identification may be accomplished outside of the device by directing the bead to a fraction collector, whereupon the test compounds present on the beads may be identified, either through identification of a tagging group, or through identification of residual compounds. Incorporation of tagging groups in combinatorial chemistry methods has been previously described using encrypted nucleotide sequences or chlorinated/fluorinated aromatic compounds as tagging groups. See, e.g., Published PCT Application No. WO 95/12608. Alternatively, the beads may be transported to a separate assay system within the device itself whereupon the identification may be carried out.

Figure 6A:
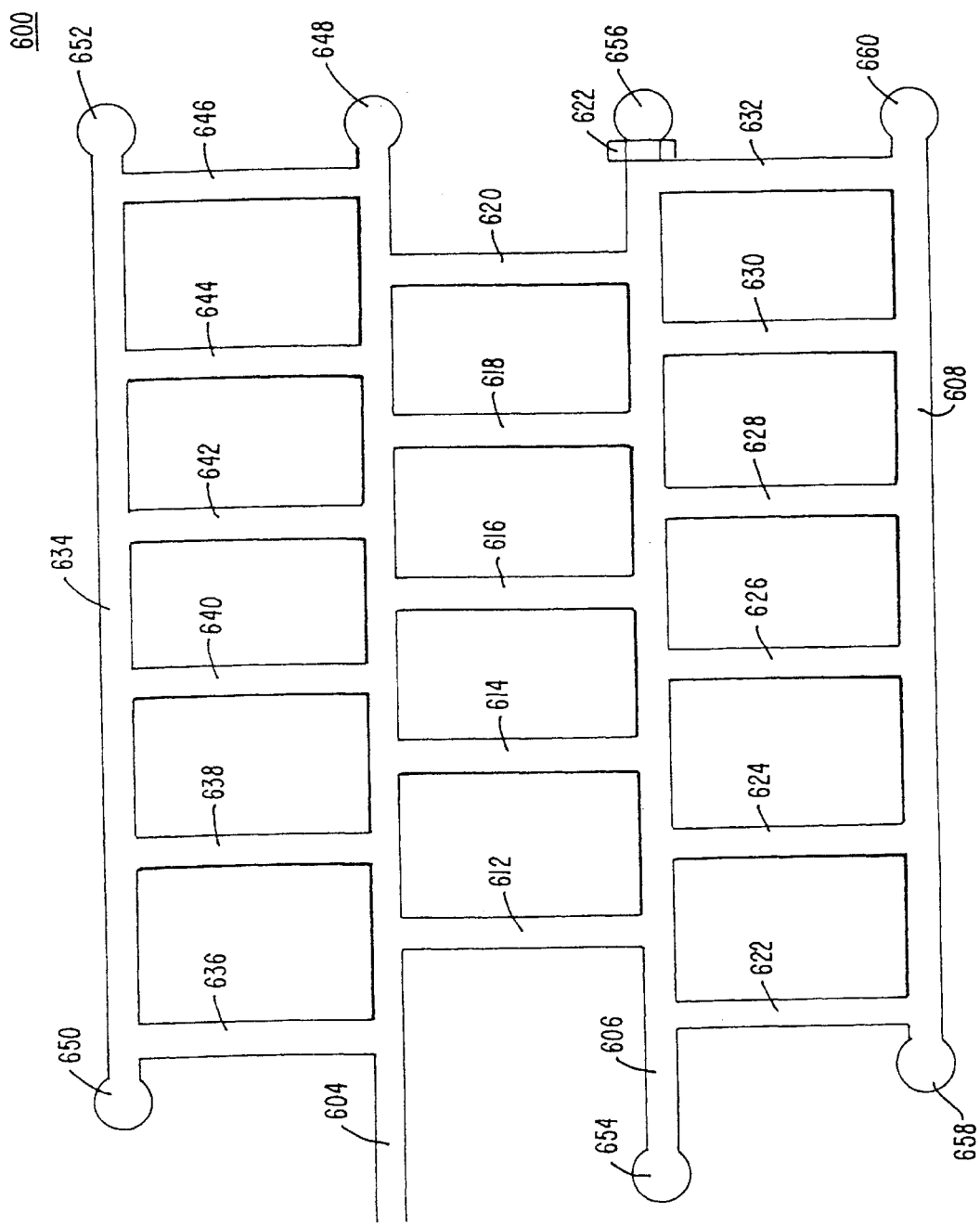
FIG. 6A shows a schematic illustration of a serial input parallel reaction device for use with fluid based test compounds.

FIG. 6A shows an alternate embodiment of a "serial input parallel reaction" device which can be used for fluid based as opposed to bead based systems. As shown the device 600 generally incorporates at least two transverse channels as were shown in FIGS. 3 and 4, namely, sample injection channel 604 and detection channel 606. These transverse channels are interconnected by the series of parallel channels 612–620 which connect sample channel 604 to detection channel 606.

The device shown also includes an additional set of channels for directing the flow of fluid test compounds into the reaction channels. In particular, an additional transverse pumping channel 634 is fluidly connected to sample channel 604 via a series of parallel pumping channels 636–646. The pumping channel includes reservoirs 650 and 652 at its termini. The intersections of parallel channels 636–646 are staggered from the intersections of parallel channels 612–620 with sample channel 604, e.g., half way between. Similarly, transverse pumping channel 608 is connected to detection channel 606 via parallel pumping channels 622–632. Again, the intersections of parallel pumping channels 622–632 with detection channel 606 are staggered from the intersections of reaction channels 612–620 with the detection channel 606.

Figure 6B:
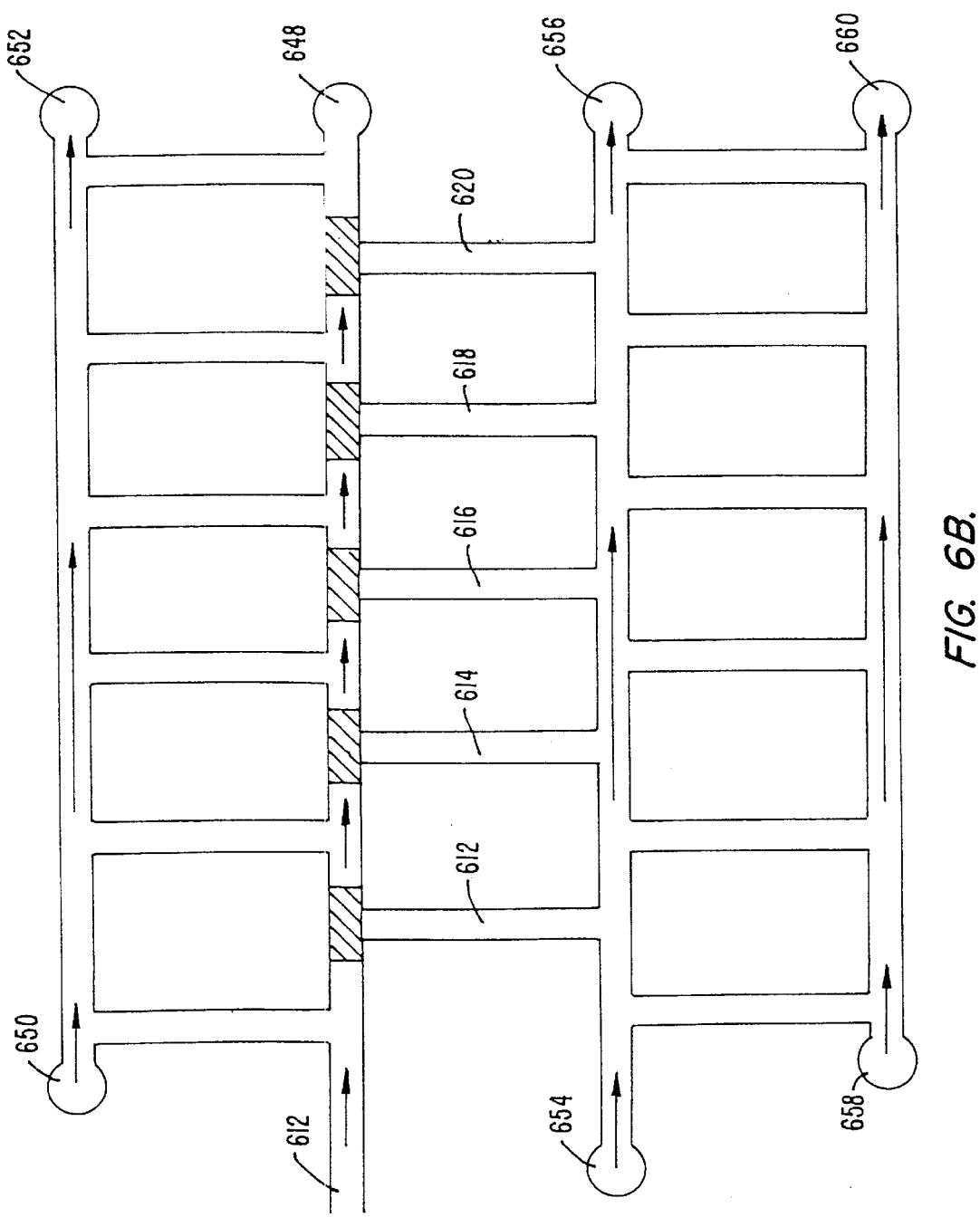
FIGS. 6B and 6C show a schematic illustration of fluid flow patterns within the device shown in FIG. 6A.
Figure 6C:
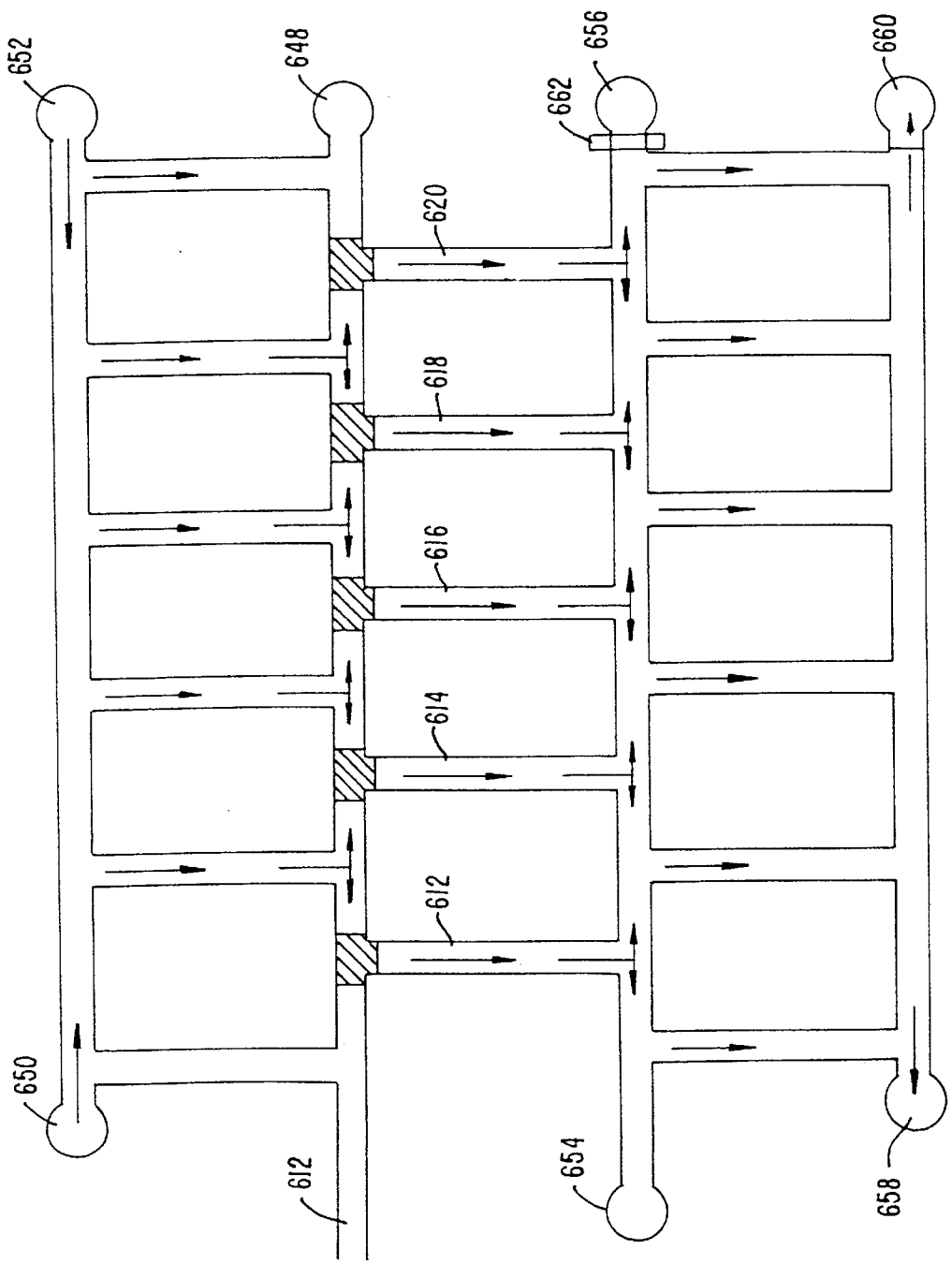

A schematic illustration of the operation of this system is shown in FIGS. 6B–6C. As shown, a series of test compounds, physically isolated from each other in separate subject material regions, are introduced into sample channel 604 using the methods described previously. For electroosmotic systems, potentials are applied at the terminus of sample channel 604, as well as reservoir 648. Potentials are also applied at reservoirs 650:652, 654:656, and 658:660. This results in a fluid flow along the transverse channels 634, 604, 606 and 608, as illustrated by the arrows, and a zero net flow through the parallel channel arrays interconnecting these transverse channels, as shown in FIG. 6B. Once the subject material regions containing the test compounds are aligned with parallel reaction channels 612–620, connecting sample channel 604 to detection channel 606, as shown by the shaded areas in FIG. 6B, flow is stopped in all transverse directions by removing the potentials applied to the reservoirs at the ends of these channels. As described above, the geometry of the channels can be varied to maximize the use of space on the substrate. For example, where the sample channel is straight, the distance between reaction channels (and thus, the number of parallel reactions that can be carried out in a size limited substrate) is dictated by the distance between subject material regions. These restrictions, however, can be eliminated through the inclusion of altered channel geometries. For example, in some aspects, the length of a first and second spacer regions can be accomodated by a serpentine, square-wave, saw tooth or other reciprocating channel geometry. This allows packing a maximum number of reaction channels onto the limited area of the substrate surface.

Once aligned with the parallel reaction channels, the sample, or subject material, is then moved into the parallel reaction channels 612–620 by applying a first potential to reservoirs 650 and 652, while applying a second potential to reservoirs 658 and 660, whereby fluid flow through parallel pumping channels 636–646 forces the subject material into parallel reaction channels 612–620, as shown in FIG. 6C. During this process, no potential is applied at reservoirs 648, 654, 656, or the terminus of sample channel 604. Parallel channels 636–646 and 622–632 are generally adjusted in length such that the total channel length, and thus the level of resistance, from reservoirs 650 and 652 to channel 604 and from reservoirs 658 and 660 to channel 606, for any path taken will be the same. Resistance can generally be adjusted by adjusting channel length or width. For example, channels can be lengthened by including folding or serpentine geometries. Although not shown as such, to accomplish this same channel length, channels 636 and 646 would be the longest and 640 and 642 the shortest, to create symetric flow, thereby forcing the samples into the channels. As can be seen, during flowing of the samples through channels 612–620, the resistance within these channels will be the same, as the individual channel length is the same.

Following the reaction to be screened, the subject material region/signal element is moved into detection channel 606 by applying a potential from reservoirs 650 and 652 to reservoirs 658 and 660, while the potentials at the remaining reservoirs are allowed to float. The subject material regions/signal are then serially moved past the detection window/detector 662 by applying potentials to reservoirs 654 and 656, while applying appropriate potentials at the termini of the other transverse channels to prevent any flow along the various parallel channels.

Although generally described in terms of screening assays for identification of compounds which affect a particular interaction, based upon the present disclosure, it will be readily appreciated that the above described microlaboratory systems may also be used to screen for compounds which specifically interact with a component of a biochemical system without necessarily affecting an interaction between that component and another element of the biochemical system. Such compounds typically include binding compounds which may generally be used in, e.g., diagnostic and therapeutic applications as targeting groups for therapeutics or marker groups, i.e. radionuclides, dyes and the like. For example, these systems may be used to screen test compounds for the ability to bind to a given component of a biochemical system.

III. Microlaboratory System

Although generally described in terms of individual discrete devices, for ease of operation, the systems described will typically be a part of a larger system which can monitor and control the functioning of the devices, either on an individual basis, or in parallel, multi-device screens. An example of such a system is shown in FIG. 7.

Figure 7:
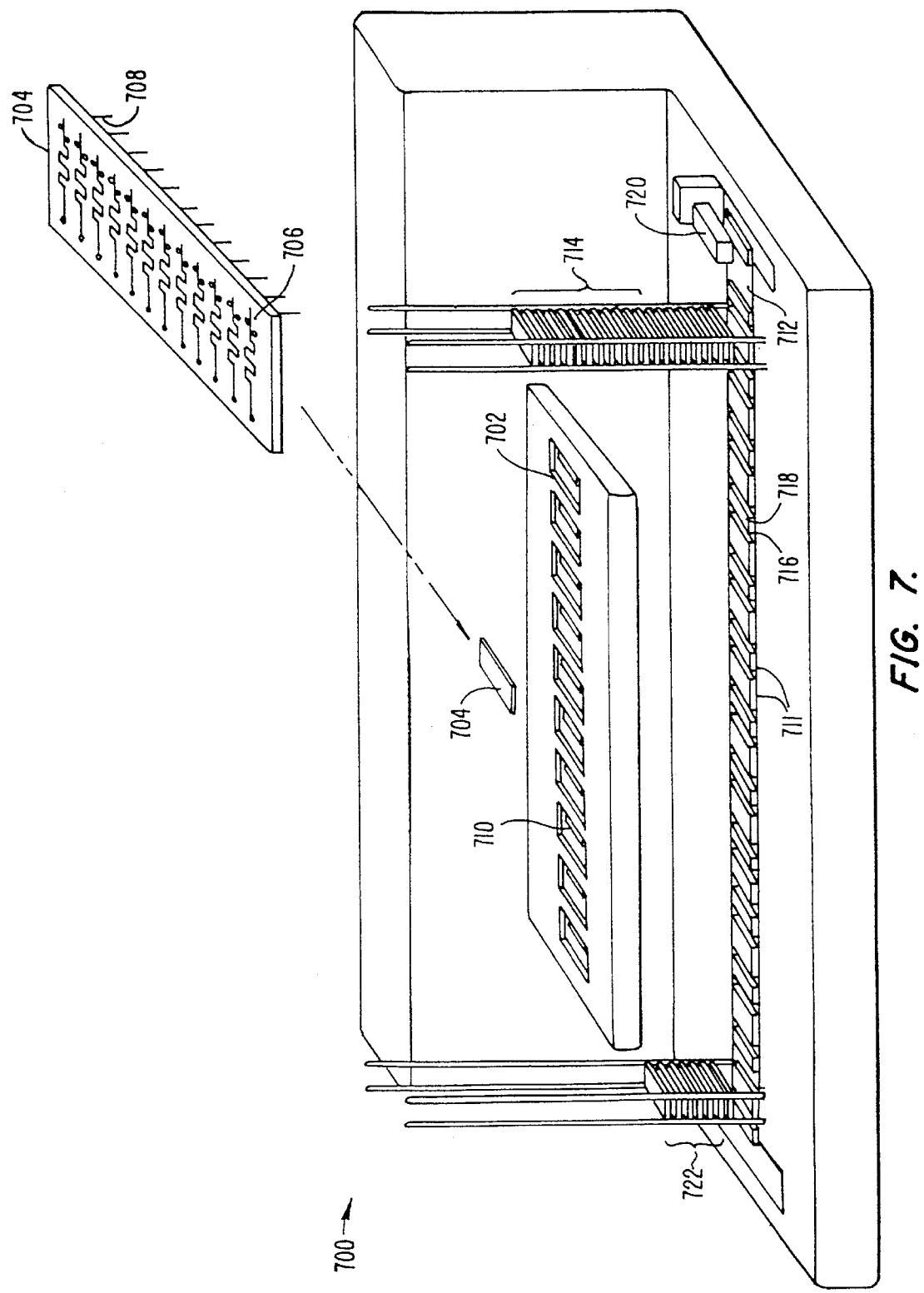
FIG. 7 shows a schematic illustration of one embodiment of an overall assay systems which employs multiple microlaboratory devices labeled as "LabChips™" for screening test compounds.

As shown in FIG. 7, the system may include a test compound processing system 700. The system shown includes a platform 702 which can hold a number of separate assay chips or devices 704. As shown, each chip includes a number of discrete assay channels 706, each having a separate interface 708, e.g., pipettor, for introducing test compounds into the device. These interfaces are used to sip test compounds into the device, separated by sipping first and second spacer fluids, into the device. In the system shown, the interfaces of the chip are inserted through an opening 710 in the bottom of the platform 702, which is capable of being raised and lowered to place the interfaces in contact with test compounds or wash/first spacer fluids/second spacer fluids, which are contained in, e.g., multiwell micro plates 711, positioned below the platform, e.g., on a conveyor system 712. In operation, multiwell plates containing large numbers of different test compounds are stacked 714 at one end of the conveyor system. The plates are placed upon the conveyor separated by appropriate buffer reservoirs 716 and 718, which may be filled by buffer system 720. The plates are stepped down the conveyor and the test compounds are sampled into the chips, interspersed by appropriate spacer fluid regions. After loading the test compounds into the chips, the multiwell plates are then collected or stacked 722 at the opposite end of the system. The overall control system includes a number of individual microlaboratory systems or devices, e.g., as shown in FIG. 7. Each device is connected to a computer system which is appropriately programmed to control fluid flow and direction within the various chips, and to monitor, record and analyze data resulting from the screening assays that are performed by the various devices. The devices will typically be connected to the computer through an intermediate adapter module which provides an interface between the computer and the individual devices for implementing operational instructions from the computer to the devices, and for reporting data from the devices to the computer. For example, the adapter will generally include appropriate connections to corresponding elements on each device, e.g., electrical leads connected to the reservoir based electrodes that are used for electroosmotic fluid flow, power inputs and data outputs for detection systems, either electrical or fiberoptic, and data relays for other sensor elements incorporated into the devices. The adapter device may also provide environmental control over the individual devices where such control is necessary, e.g., maintaining the individual devices at optimal temperatures for performing the particular screening assays.

As shown, each device is also equipped with appropriate fluid interfaces, e.g., micropipettors, for introducing test compounds into the individual devices. The devices may be readily attached to robotic systems which allow test compounds to be sampled from a number of multiwell plates that are moved along a conveyor system. Intervening spacer fluid regions can also be introduced via a spacer solution reservoir.

EXAMPLES

Example 1—Enzyme Inhibitor Screen

Figure 8:
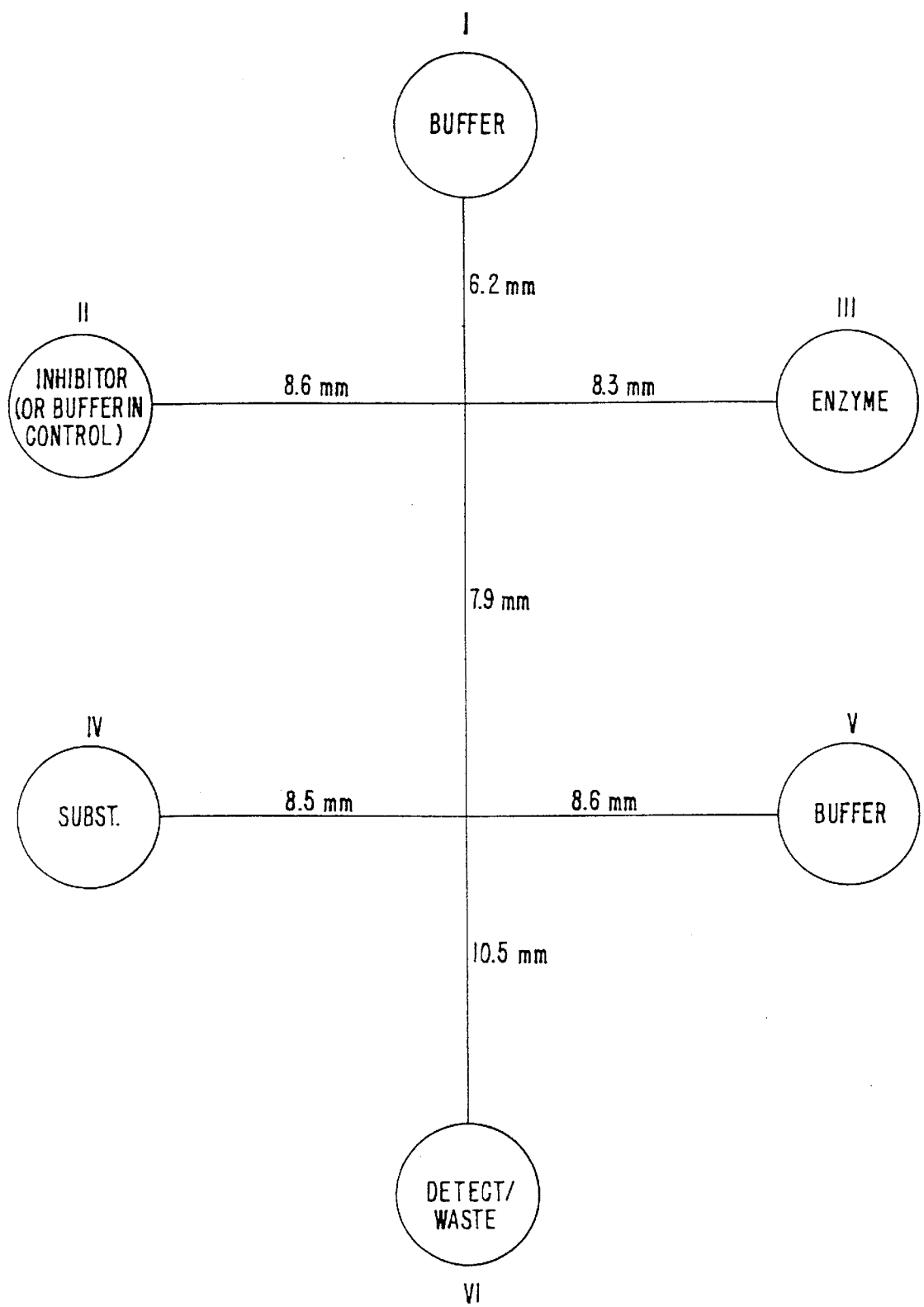
FIG. 8 is a schematic illustration of a chip layout used for a continuous-flow assay screening system.

The efficacy of performing an enzyme inhibition assay screen was demonstrated in a planar chip format. A 6-port planar chip was employed having the layout shown in FIG. 8. The numbers adjacent the channels represent the lengths of each channel in millimeters. Two voltage states were applied to the ports of the chip. The first state (State 1) resulted in flowing of enzyme with buffer from the top buffer well into the main channel. The second voltage state (State 2) resulted in the interruption of the flow of buffer from the top well, and the introduction of inhibitor from the inhibitor well, into the main channel along with the enzyme. A control experiment was also run in which buffer was placed into the inhibitor well.

Applied voltages at each port for each of the two applied voltage states were as follows:

|  | State 1 | State 2 |
|---|---|---|
| Top Buffer Well (I) | 1831 | 1498 |
| Inhibitor Well (II) | 1498 | 1900 |
| Enzyme Well (III) | 1891 | 1891 |
| Substrate Well (IV) | 1442 | 1442 |
| Bottom Buffer Well (V) | 1442 | 1442 |
| Detect./Waste Well (VI) | 0 | 0 |

To demonstrate the efficacy of the system, an assay was designed to screen inhibitors of β-galactosidase using the following enzyme/substrate/inhibitor reagents:

| | |
|---|---|
| Enzyme: | β-Galactosidase (180 U/ml in 50 mM Tris/ 300 μg/ml BSA |
| Substrate: | Fluorescein-digalactoside (FDG) 400 μM |
| Inhibitor: | IPTG, 200 mM |
| Buffer: | 20 mM Tris, pH 8.5 |

Figure 9A:
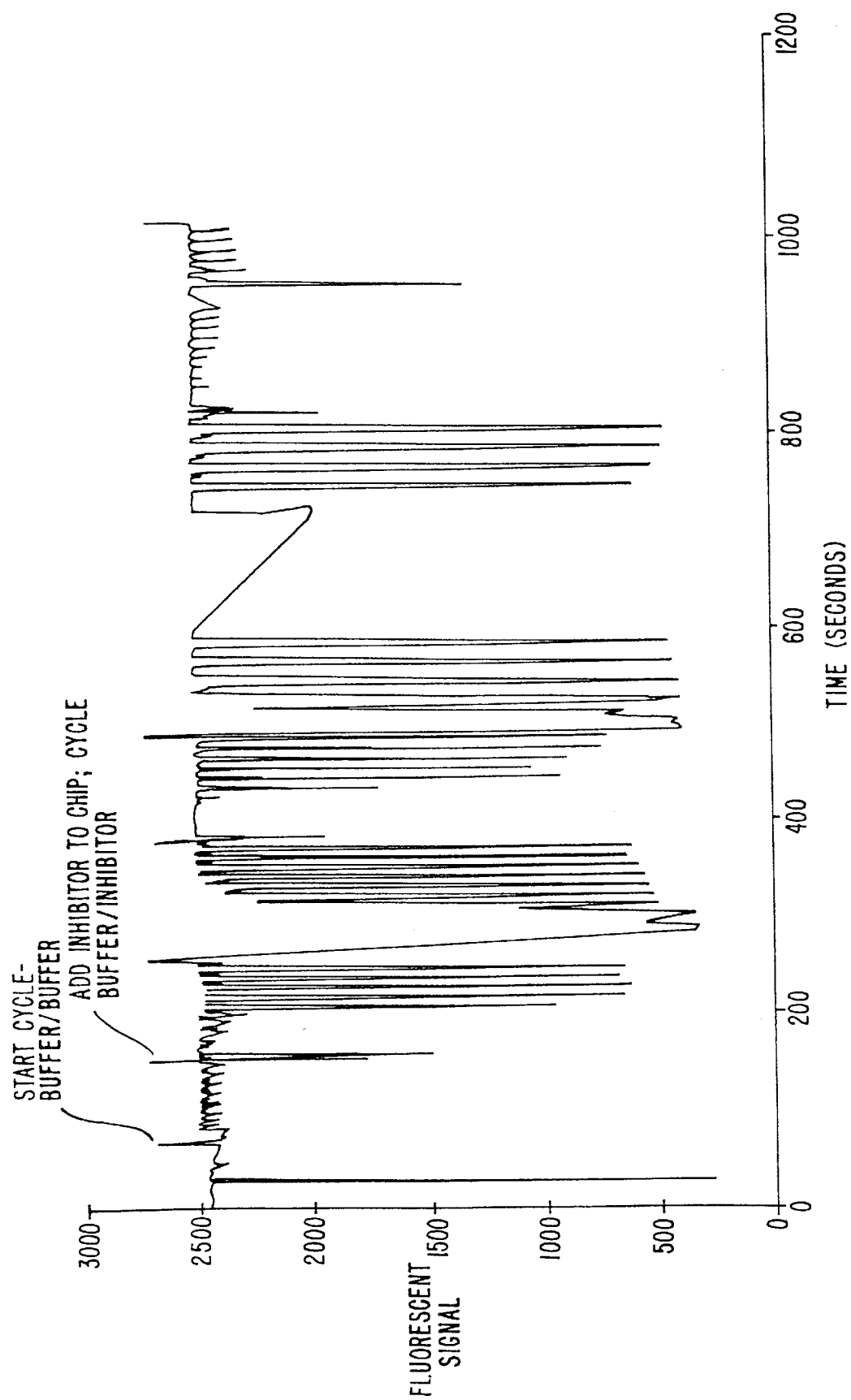
FIG. 9A shows fluorescence data from a test screen which periodically introduced a known inhibitor (IPTG) into a β-galactosidase assay system in a chip format.
Figure 9B:
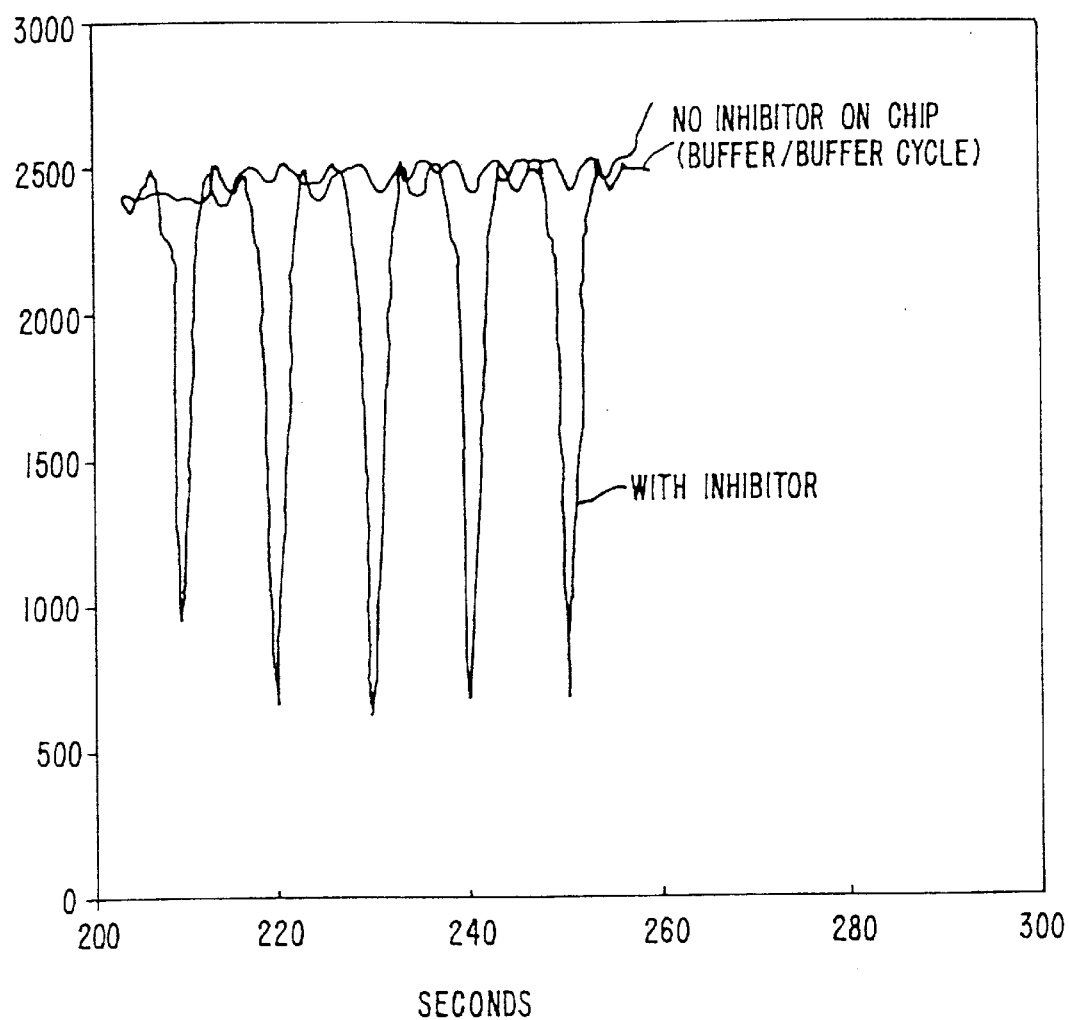
FIG. 9B shows a superposition of two data segments from FIG. 9A, directly comparing the inhibitor data with control (buffer) data.

Enzyme and substrate were continually pumped through the main channel from their respective ports under both voltage states. Inhibitor or Buffer were delivered into the main channel alternately from their respective wells by alternating between voltage state 1 and voltage state 2. When no inhibitor was present at the detection end of the main channel, a base line level of fluorescent product was produced. Upon introduction of inhibitor, the fluorescent signal was greatly reduced, indicating inhibition of the enzyme/substrate interaction. Fluorescent data obtained from the alternating delivery of inhibitor and buffer into the main channel is shown in FIG. 9A. FIG. 9B a superposition of the two data segments from FIG. 9A, directly comparing the inhibitor data with control (buffer) data. The control shows only a minor fluctuation in the fluorescent signal that apparently resulted from a dilution of the enzyme substrate mixture, whereas the inhibitor screen shows a substantial reduction in the fluorescent signal, indicating clear inhibition.

Example 2—Screening of Multiple Test Compounds

Figure 10:
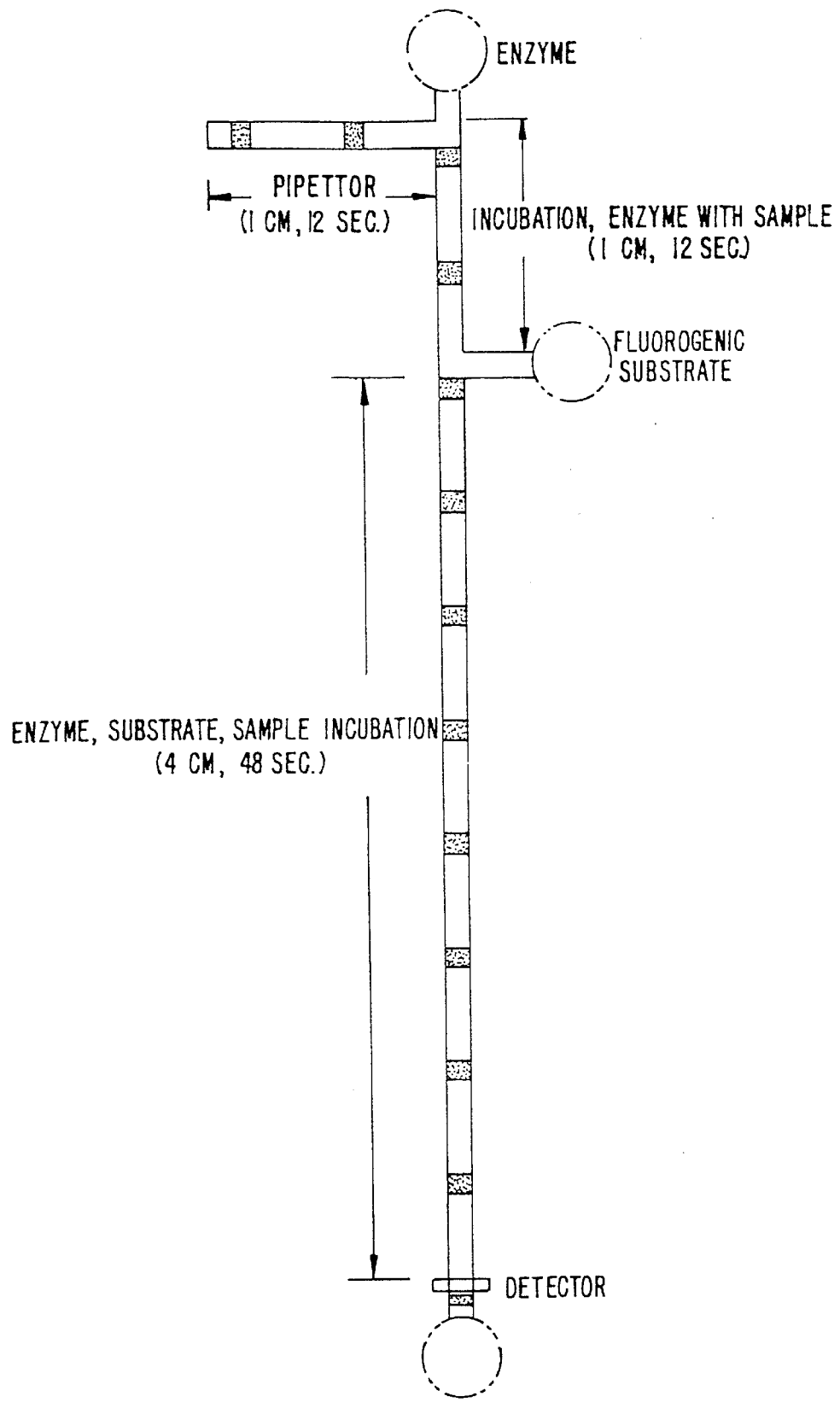
FIG. 10 illustrates the operating parameters of a fluid flow system on a small chip device for performing enzyme inhibitor screening.

An assay screen is performed to identify inhibitors of an enzymatic reaction. A schematic of the chip to be used is shown in FIG. 10. The chip has a reaction channel 5 cm in length which includes a 1 cm incubation zone and a 4 cm reaction zone. The reservoir at the beginning of the sample channel is filled with enzyme solution and the side reservoir is filled with the fluorogenic substrate. Each of the enzyme and substrate are diluted to provide for a steady state signal in the linear signal range for the assay system, at the detector. Potentials are applied at each of the reservoirs (sample source, enzyme, substrate and waste) to achieve an applied field of 200 V/cm. This applied field produces a flow rate of 2 mm/second. During passage of a given sample through the chip, there will generally be a diffusive broadening of the sample. For example, in the case of a small molecule sample, e.g., 1 mM benzoic acid diffusive broadening of approximately 0.38 mm and an electrophoretic shift of 0.4 mm is seen.

Figure 11:
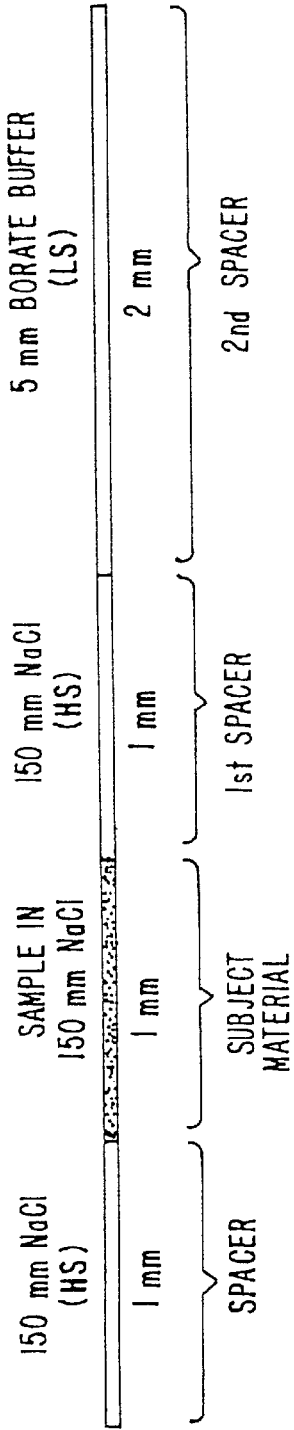
FIG. 11 shows a schematic illustration of timing for sample/spacer loading in a microfluidic device channel.
Figure 11:
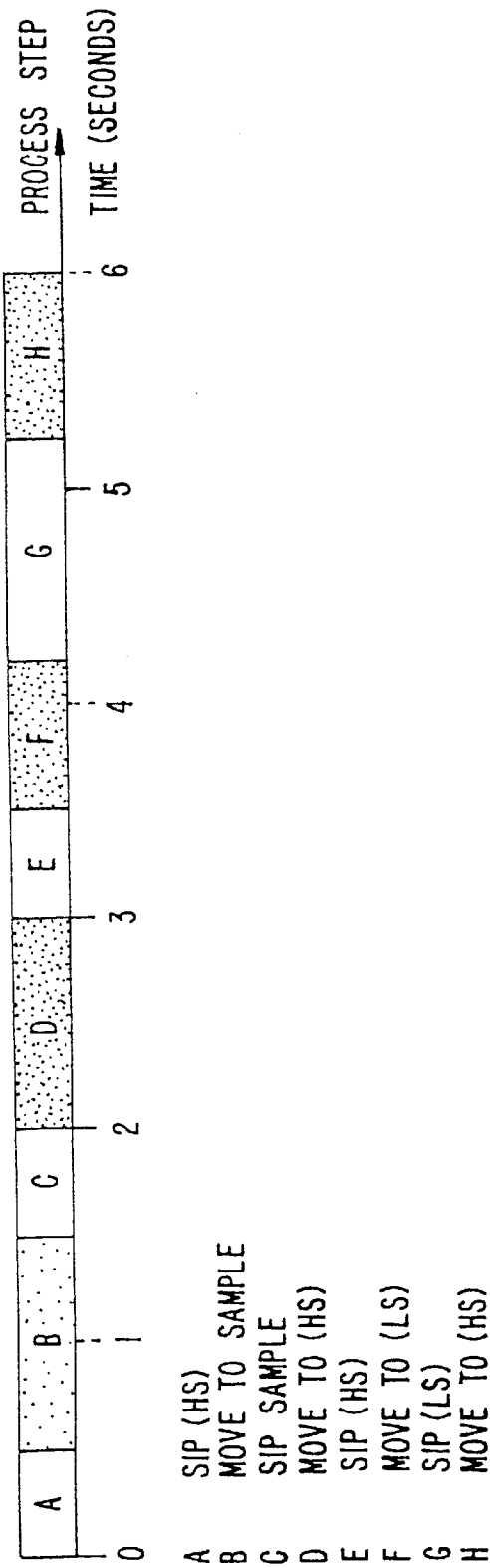

Subject material regions containing test compounds in 150 mM NaCl are introduced into the sample channel separated by first spacer regions of 150 mM NaCl and second spacer regions of 5 mM borate buffer. Once introduced into the sample channel shown, the subject material region requires 12 seconds to travel the length of the sample channel and reach the incubation zone of the reaction channel. This is a result of the flow rate of 2 mm/sec, allowing for 1 second for moving the sample pipettor from the sample to the spacer compounds. Allowing for these interruptions, the net flow rate is 0.68 mm/sec. Another 12 seconds is required for the enzyme/test compound mixture to travel through the incubation zone to the intersection with the substrate channel where substrate is continuously flowing into the reaction zone of the reaction channel. Each subject material region containing the test compounds then requires 48 seconds to travel the length of the reaction zone and past the fluorescence detector. A schematic of timing for subject material region/spacer region loading is shown in FIG. 11. The top panel shows the subject material/first spacer region/second spacer region distribution within a channel, whereas the lower panel shows the timing required for loading the channel. As shown, the schematic includes the loading (sipping) of high salt (HS) first spacer fluid ("A"), moving the pipettor to the sample or subject material ("B"), sipping the sample or subject material ("C"), moving the pipettor to the high salt first spacer fluid ("D") sipping the first spacer fluid ("E"), moving the pipettor to the low salt (LS) or second spacer fluid ("F"), sipping the second spacer fluid ("G") and returning to the first spacer fluid ("H"). The process is then repeated for each additional test compound.

A constant base fluorescent signal is established at the detector in the absence of test compounds. Upon introduction of the test compounds, a decrease in fluorescence is seen similar to that shown in FIGS. 9A and 9B, which, based upon time delays, corresponds to a specific individual test compound. This test compound is tentatively identified as an inhibitor of the enzyme, and further testing is conducted to confirm this and quantitate the efficacy of this inhibitor.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. An apparatus for screening test compounds for an effect on a flowing biochemical system, comprising:

a substrate having at least one surface;

at least two intersecting channels fabricated into said surface of said substrate, at least one of said at least two intersecting channels having at least one cross-sectional dimension in the range from about 0.1 to about 500 μm;

a source of a plurality of different test compounds fluidly connected to a first of said at least two intersecting channels;

a source of at least one component of said biochemical system fluidly connected to a second of said at least two intersecting channels;

a fluid direction system for flowing said at least one component within said second of said at least two intersecting channels and for flowing said different test compounds from said first to said second of said at least two intersecting channels;

a cover mated with said surface; and a detection zone in said second channel for detecting an effect of said test compound on said flowing biochemical system.

2. The apparatus of claim 1, wherein said fluid direction system generates a continuous flow of said at least one component along said second of said at least two intersecting channels, and periodically injects a test compound from said first channel into said second channel.

3. The apparatus of claim 1, further comprising a source of a second component of said biochemical system, and a third channel fabricated into said surface, said third channel fluidly connecting at least one of said at least two intersecting channels with said source of said second component of said biochemical system.

4. The apparatus of claim 3, wherein said fluid direction system generates a continuous flow of a mixture of said at least one component and said second component along said second of said at least two intersecting channels, and periodically ejects a test compound from said first channel into said second channel.

5. The apparatus of claim 1, wherein said fluid direction system continuously flows said plurality of different test compounds from said first into said second of said at least two intersecting channels, each of said plurality of different test compounds being separated by a fluid spacer.

6. The apparatus of claim 1, wherein said fluid direction system comprises:
   at least tree electrodes, each electrode being in electrical contact with said at least two intersecting channels on a different side of an intersection formed by said at least two intersecting channels; and
   a control system for concomitantly applying a variable voltage at each of said electrodes, whereby movement of said test compounds or said at least one component in said at least two intersecting channels may be controlled.

7. The apparatus of claim 1, wherein said detection system includes a detection window in said second channel.

8. The apparatus of claim 7, wherein said detection system is a fluorescent detection system.

9. The apparatus of claim 1, wherein said substrate is planar.

10. The apparatus of claim 1, wherein said substrate comprises etched glass.

11. The apparatus of claim 1, wherein said substrate comprises etched silicon.

12. The apparatus of claim 1, further comprising an insulating layer disposed over said etched silicon substrate.

13. The apparatus of claim 1, wherein said substrate is a molded polymer.

14. The apparatus of claim 1, wherein said at least one component of a biochemical system comprises an enzyme, and an enzyme substrate which produces a detectable signal when reacted with said enzyme.

15. The apparatus of claim 14, wherein said enzyme substrate is selected from the group consisting of chromogenic and fluorogenic enzyme substrates.

16. The apparatus of claim 1, wherein said at least one component of a biochemical system comprises a receptor/ligand binding pair, wherein at least one of said receptor or ligand has a detectable signal associated therewith.

17. The apparatus of claim 1, wherein said at least one component of a biochemical system comprises a receptor/ligand binding pair, wherein binding of said receptor to said ligand produces a detectable signal.

18. An apparatus for detecting an effect of a test compound on a flowing biochemical system, comprising:
    a substrate having at least one surface;
    a plurality of reaction channels fabricated into said surface;
    at least two transverse channels fabricated into said surface, each of said plurality of reaction channels being fluidly connected to a first of said at least two transverse channels at a first point in said reaction channels, and fluidly connected to a second of said at least two transverse channels at a second point in said reaction channels, said at least two transverse channels and said plurality of reaction channels each having at least one cross-sectional dimension in the range from about 0.1 to about 500 $\mu$m;
    a source of at least one component of said biochemical system, said source of at least one component of said biochemical system being fluidly connected to each of said plurality of reaction channels;
    a source of test compounds fluidly connected to said first of said at least two transverse channels;
    a fluid direction system for controlling movement of said test compound and said at least one component within said at least two transverse channels and said plurality of reaction channels;
    a cover mated with said surface; and
    a detection system for detecting an effect of said test compound on said flowing biochemical system.

19. The apparatus of claim 18, wherein said fluid control system comprises:
    a plurality of individual electrodes, each in electrical contact with each terminus of said at least two transverse channels; and
    a control system for concomitantly applying a variable voltage at each of said electrodes, whereby movement of said test compounds or said at least first component in said at least two transverse channels and said plurality of reaction channels may be controlled.

20. The apparatus of claim 18, wherein each of said plurality of reaction channels comprises a bead resting well at said first point in said plurality of reaction channels.

21. The apparatus of claim 18, wherein said source of at least one component of a biochemical system is fluidly connected to said plurality of reaction channels by a third transverse channel, said third transverse channel having at least one cross sectional dimension in a range of from 0.1 to 500 $\mu$m and being fluidly connected to each of said plurality of reaction channels at a third point in said reaction channels.

22. The apparatus of claim 21, wherein said third point in said reaction channels is intermediate to said first and second points in said reaction channels.

23. The apparatus of claim 22, further comprising a particle retention zone in each of said plurality of reaction channels, between said third and said second points in said plurality of reaction channels.

24. The apparatus of claim 23, wherein said particle retention zone comprises a particle retention matrix.

25. The apparatus of claim 23, wherein said particle retention zone comprises a microstructural filter.

26. The apparatus of claim 18, wherein said plurality of reaction channels comprises a plurality of parallel reaction channels fabricated into said surface of said substrate and said at least two transverse channels are connected at opposite ends of each of said parallel reaction channels.

27. The apparatus of claim 18, wherein said at least two transverse channels are fabricated on said surface of said substrate in inner and outer concentric channels, respectively, and said plurality of reaction channels extend radially from said inner concentric channel to said outer concentric channel.

28. The apparatus of claim 27, wherein said detection system comprises a detection window in said second channel.

29. The apparatus of claim 28, wherein said detection system is a fluorescent detection system.

30. The apparatus of claim 18, wherein said substrate is planar.

31. The apparatus of claim 18, wherein said substrate comprises etched glass.

32. The apparatus of claim 18, wherein said substrate comprises etched silicon.

33. The apparatus of claim 18, further comprising an insulating layer disposed over said etched silicon substrate.

34. The apparatus of claim 18, wherein said substrate is a molded polymer.

35. The apparatus of claim 18, wherein said at least one component of a biochemical system comprises an enzyme, and an enzyme substrate which produces a detectable signal when reacted with said enzyme.

36. The apparatus of claim 35, wherein said enzyme substrate is selected from the group consisting of chromogenic and fluorogenic substrates.

37. The apparatus of claim 18, wherein said at least one component of a biochemical system comprises a receptor/ligand binding pair, wherein at least one of said receptor or ligand has a detectable signal associated therewith.

38. The apparatus of claim 18, wherein said at least one component of a biochemical system comprises a receptor/ligand binding pair, wherein binding of said receptor to said ligand produces a detectable signal.

* * * * *

UNITED STATES PATENT AND TRADEMARK OFFICE
CERTIFICATE OF CORRECTION

PATENT NO : 6,046,056
DATED : April 4, 2000
INVENTOR(S): John Wallace Parce, et al.

It is certified that error appears in the above-identified patent and that said Letters Patent are hereby corrected as shown below:

In claim 6, at line 3:

--tree-- should read as --three--

Signed and Sealed this

Fifteenth Day of May, 2001

Attest:

NICHOLAS P. GODICI

Attesting Officer

Acting Director of the United States Patent and Trademark Office